United States Patent
Mousa

(10) Patent No.: US 9,822,190 B2
(45) Date of Patent: Nov. 21, 2017

(54) COMPOSITIONS AND METHOD FOR ANTI-SICKLING OF RED BLOOD CELLS IN SICKLE CELL DISEASE

(71) Applicant: Shaker A. Mousa, Wynantskill, NY (US)

(72) Inventor: Shaker A. Mousa, Wynantskill, NY (US)

( * ) Notice: Subject to any disclaimer, the term of this patent is extended or adjusted under 35 U.S.C. 154(b) by 0 days.

(21) Appl. No.: 15/008,947

(22) Filed: Jan. 28, 2016

(65) Prior Publication Data
US 2016/0222137 A1    Aug. 4, 2016

Related U.S. Application Data

(60) Provisional application No. 62/109,099, filed on Jan. 29, 2015.

(51) Int. Cl.
| | | |
|---|---|---|
| *A61K 9/48* | (2006.01) | |
| *C08B 37/00* | (2006.01) | |
| *A61K 31/727* | (2006.01) | |
| *A61K 9/19* | (2006.01) | |
| *A61K 45/06* | (2006.01) | |
| *A61K 9/51* | (2006.01) | |
| *C08B 37/08* | (2006.01) | |

(52) U.S. Cl.
CPC ............ *C08B 37/0075* (2013.01); *A61K 9/19* (2013.01); *A61K 9/5123* (2013.01); *A61K 31/727* (2013.01); *A61K 45/06* (2013.01); *C08B 37/003* (2013.01)

(58) Field of Classification Search
CPC . C08B 37/0075; C08B 37/003; A61K 31/727; A61K 45/06
See application file for complete search history.

(56) References Cited

U.S. PATENT DOCUMENTS

| | | | | |
|---|---|---|---|---|
| 7,829,708 B2 * | 11/2010 | Roberts | ................ | C07D 239/95 544/283 |
| 2012/0129916 A1 * | 5/2012 | Peer | ..................... | A61K 9/1272 514/44 A |
| 2012/0195957 A1 * | 8/2012 | Sachdeva | ............. | A61K 31/192 424/450 |

OTHER PUBLICATIONS

Hirsh; title: Low Molecular Weight Heparin; Circulation; vol. 98, pp. 1575-1582; originally published Oct. 13, 1998.*
MPBio, title: poly-L_lysine; product information; downloaded from http://www4.mpbio.com/ecom/docs/proddata.nsf/(webtds2)/150175, Apr. 7, 2017.*
Serjent GR. Sickle cell disease. 3rd edition. New York: Oxford University Press; 2001. Homozygous sickle cell disease; pp. 429-435.
Pauling L, Itano HA. Sickle cell anemia a molecular disease. Science. 1949; 110:543-8.
Ingram VM. Gene mutations in human hemoglobin: The chemical difference between normal and sickle cell hemoglobin. Nature. 1957; 180:326-8.
Report by the Secretariat, 117th session of Executive Board (EB117/34) Geneva: World Health Organization; 2005. WHO. Sickle cell anemia; p. 1.
Jain SK, Shohet SB. A novel phospholipid in irreversibly sickled cells: Evidence for in vivo peroxidative membrane damage in sickle cell disease. Blood. 1984; 63:362-7.
Lachant NA, Tanaka KR. Antioxidants in sickle cell disease: The in vitro effects of ascorbic acid. Am J Med Sci. 1986; 292:3-10.
Alvarez O, Montague NS, Marin M, O'Brien R, Rodriguez MM. Quantification of Sickle Cells in the Peripheral Smear as a Marker of Disease Severity. Fetal Pediatr Pathol. .Jun. 2005; 34(3):149-54.

* cited by examiner

*Primary Examiner* — Yanzhi Zhang
(74) *Attorney, Agent, or Firm* — Schmeiser, Olsen & Watts, LLP

(57) ABSTRACT

A nano-composition that includes nanoparticles, a method of forming the nano-composition, and a method of using the composition. The nanoparticles include a polycationic polymer ionically bonded to one or more polyanionic Glycosaminoglycans (GAGs), wherein the polycationic polymer is chitosan, methylated chitosan, poly L-Lysine, or poly L-Arginine.

19 Claims, 28 Drawing Sheets m = 1 to 25, R = H or $SO_3Na$, R1 = H, $SO_3Na$ or $COCH_3$, R2 = H and R3 = COONa or R2 = COONa and R3 = H Figure 2: Synthesis of tri-methylated chitosan (TMC) from chitosan Figure 3: Encapsulation of 80 mg from the LMWH Tinzaparin into Chitosan Nanoparticles m = 1 to 25, R = H or SO$_3$Na, R1 = H, SO$_3$Na or COCH$_3$, R2 = H and R3 = COONa or R2 = COONa and R3 = H, and N-(3-Dimethylaminopropyl)
- N'-ethylcarbodiimide hydrochloride = EDC m = 1 to 25, R = H or SO$_3$Na, R1 = H, SO$_3$Na or COCH$_3$, R2 = H and R3 = COONa or R2 = COONa and R3= H, and N-(3-Dimethylaminopropyl)
-N'-ethylcarbodiimide hydrochloride = EDC m = 1 to 25, R = H or SO$_3$Na, R1 = H, SO$_3$Na or COCH$_3$, R2 = H and R3 = COONa or R2 = COONa and R3 = H, and N-(3Dimethylaminopropyl)
-N'-ethylcarbodiimide hydrochloride = EDC Figure 7: Encapsulation of S-NACH into Chitosan Nanoparticles R1= H, SO₃Na or COCH₃, R2 = H or Ac or SO₃Na and R3= Na⁺ or H, N-(3-Dimethylaminopropyl)-N'-ethylcarbodiimide hydrochloride = EDC Figure 12: Representative Thrombelastograph Figure 13: Thrombelastography (TEG) analysis of sickle disease patients Figure 14: Effect of S-NACH, 5-HMF*, L-glutamine & Thymoquinone on sickle cell blood - TEG analysis

* 5-hydroxymethyl-2-furfural

Figure 15: Representative Blood film showing sickle RBC in SCD

Figure 16: Potent anti-sickling effect of S-NACH on sickle RBC

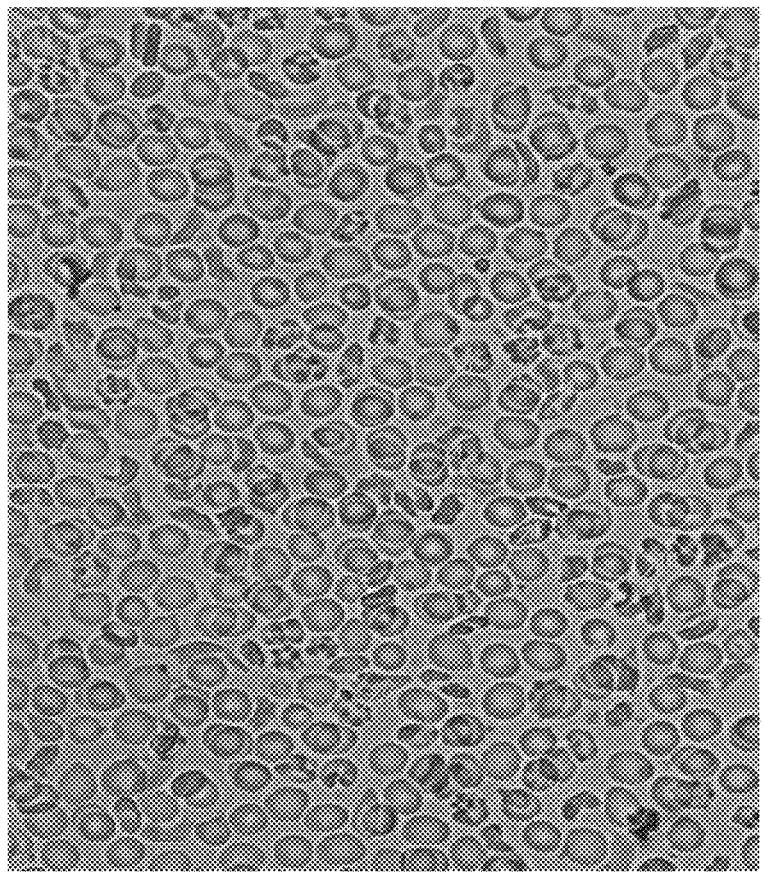
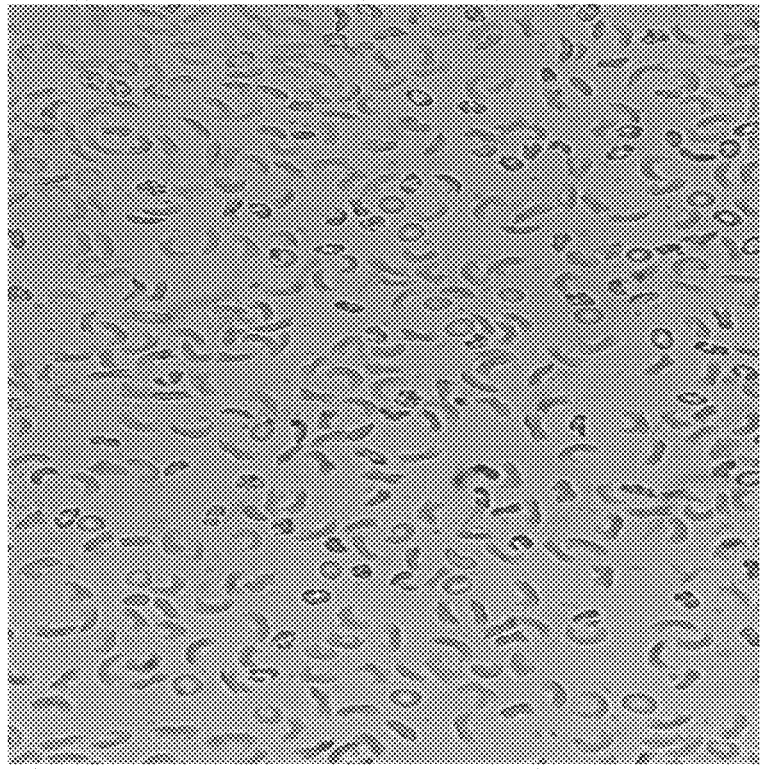
Figure 17

Figure 20
Patient 2
Incubation at 25 C
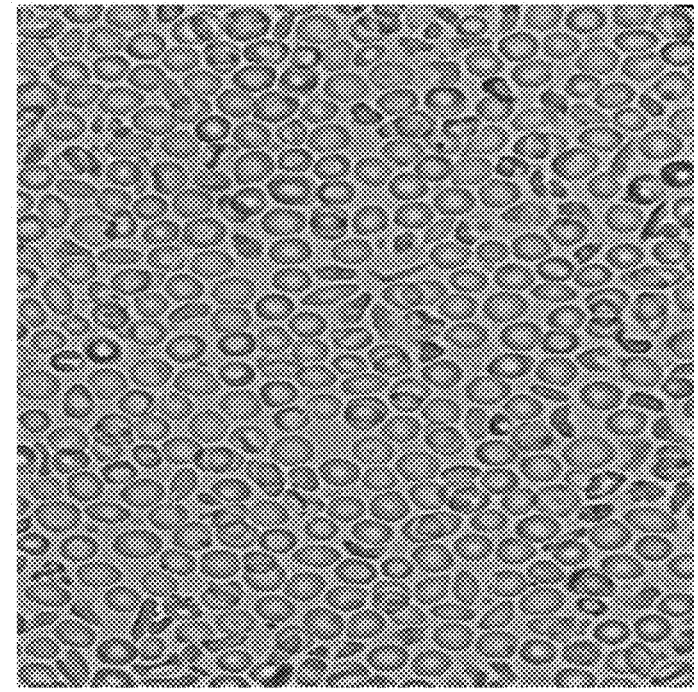
PBS
Red arrow = Sickled cell
Green arrow = Normal cell
*Percentage of sickle cell (59 %)*
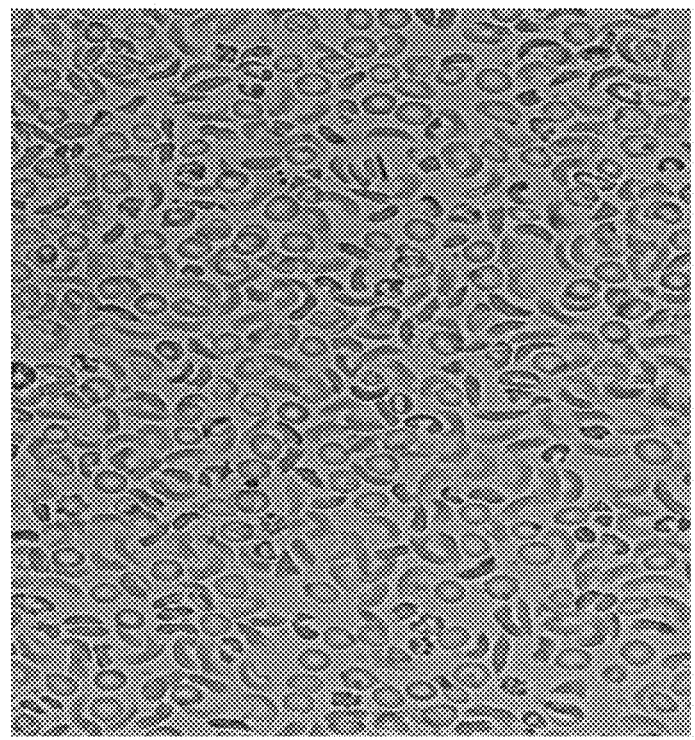
SNACH
Red arrow = Sickled cell
Green arrow = Normal cell
*Percentage of sickle cell (3.7 %)*

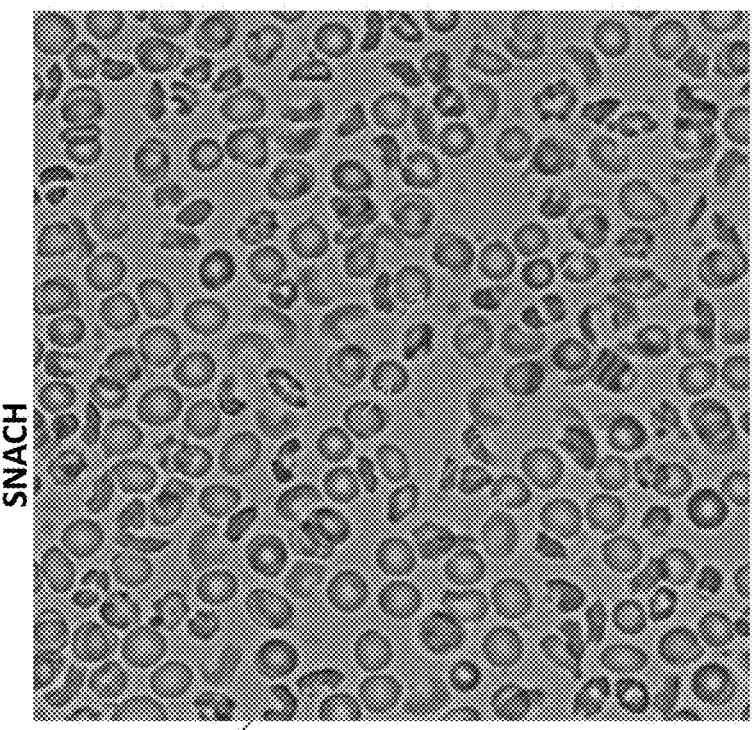
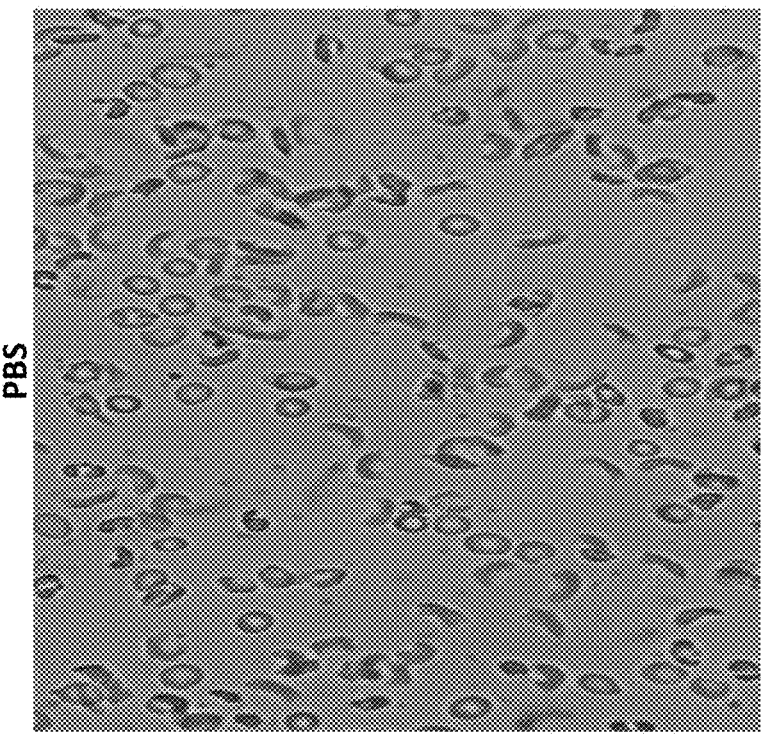
Patient 3
Incubation at 25 C
Figure 21

Figure 22
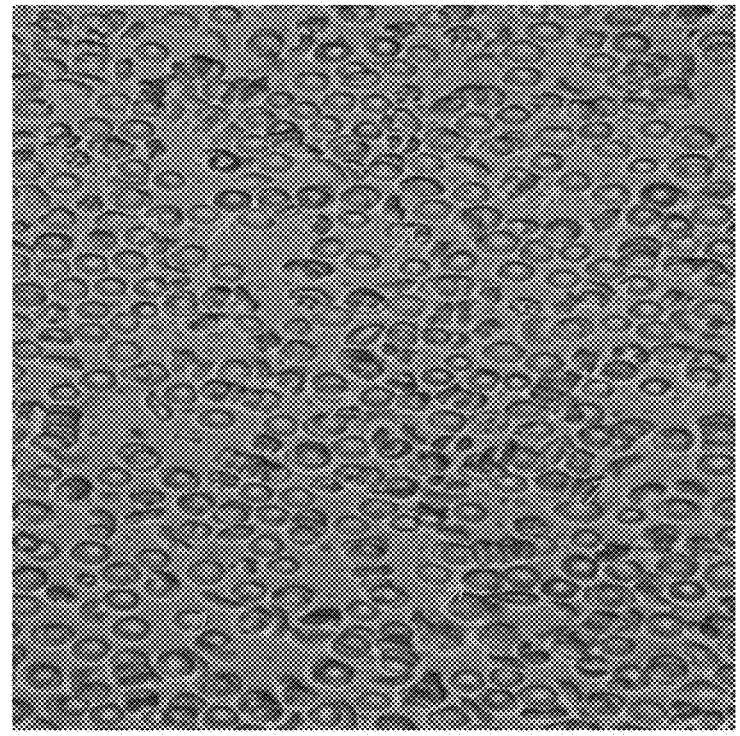
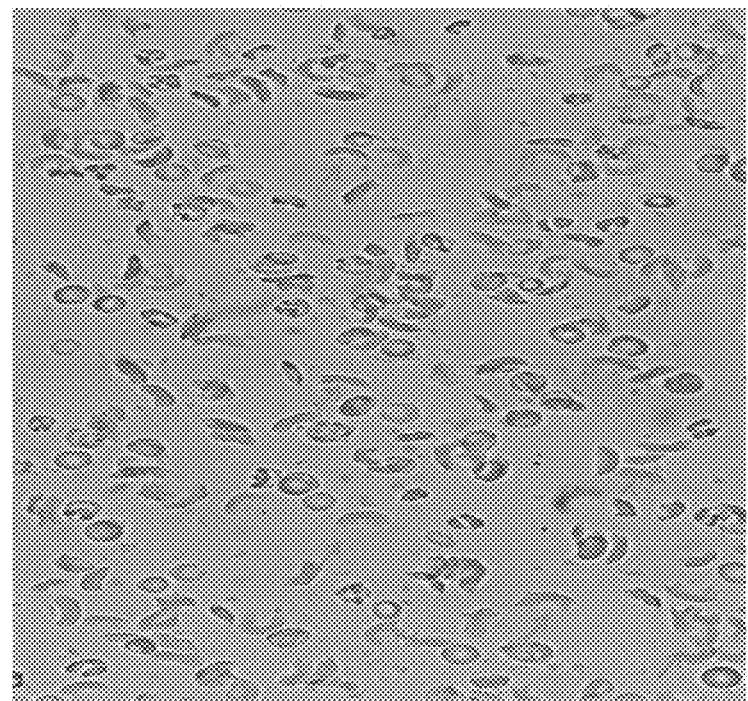
Patient 4
Incubation at 25 C

Figure 27
Control 2
Incubation at 25 C
PBS 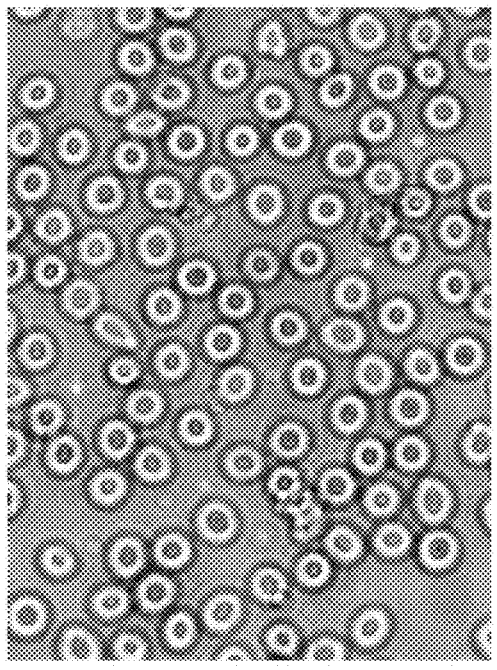 SNACH 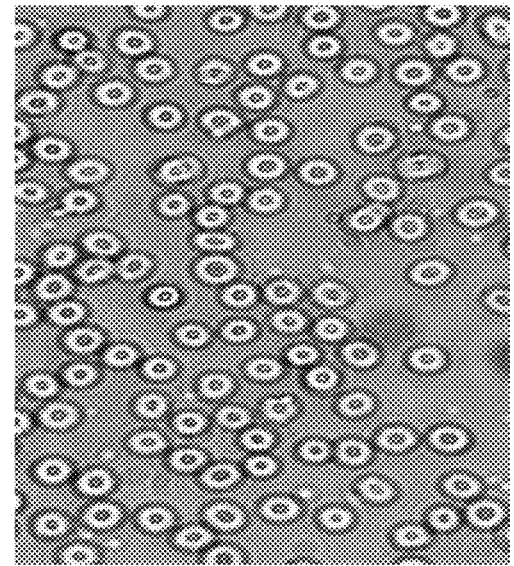
*RBCs morphology:-* Normal RBCs morphology with central pallor around 1/3 of the RBC's volume and normal borders.
*Conclusion:-* In comparison between incubation with PBS and SNACH, SNACH mostly has no pathological effect to RBCs.

# COMPOSITIONS AND METHOD FOR ANTI-SICKLING OF RED BLOOD CELLS IN SICKLE CELL DISEASE

RELATED APPLICATIONS

The present invention claims priority to U.S. Provisional No. 62/109,099, filed on Jan. 29, 2015, which is incorporated herein by reference in its entirety.

TECHNICAL FIELD

The present invention relates to a composition and associated method for use in prevention and reversal of red blood sickling in sickle disease subjects.

BACKGROUND

Sickle cell disease (SCD) is a genetic blood disorder characterized by red blood cells (RBCs) that assume an abnormal rigid sickle shape. Sickling decreases the RBCs flexibility and results in a risk of various complications (Serjent G R. Sickle cell disease, 3rd edition, New York: Oxford University Press; 2001, Homozygous sickle cell disease; pp. 429-35). Sickle cell disease is the most prevalent human hereditary disorder with prominent morbidity and mortality. Sickle cell disease is due to the change of an amino acid in position six within the beta globin chain of hemoglobin molecule, whereby glutamic acid, a polar amino acid is replaced by valine, a non-polar amino acid (Pauling L, Itano, H A., Sickle cell anemia a molecular disease, Science. 1949; 110:543-8); (Ingram V M., Gene mutations in human hemoglobin: The chemical difference between normal and sickle cell hemoglobin, Nature, 1957; 180:326-8). The amino acid change is due to the defective gene (mutation) in chromosome 11. At low oxygen tension, the mutant hemoglobin polymerizes inside the RBCs into a gel or further into fibers leading to a drastic decrease in the red cell deformability. Polymerization and precipitation of sickle hemoglobin (HbS) within the erythrocytes cause the change of shape from the normal spherical form into the one resembling a sickle, hence the name sickle cell.

The SCD has been reported to be wide spread in Africa, Jamaica, Central India, Saudi Arabia, Greece and Italy and also among Africans in America and Britain. SCD affects millions of people throughout the world (Report by the Secretariat; 117th session of Executive Board (EB117/34) Geneva: World Health Organization; 2005, WHO, Sickle cell anemia; p. 1). Clinical symptoms of patients suffering from the disease vary widely some suffer from a variety of life threatening complications. The main clinical symptoms are anemia; mild jaundice, repeated vasooclusive crises, hepatosplenomegaly, acute chest syndrome; bone, joint pain, growth retardation, and other secondary complications (Serjent G R. Sickle cell disease, 3rd edition, New York: Oxford University Press; 2001, Homozygous sickle cell disease; pp. 429-35).

The health-care cost of the management of SCD patients is disproportionately high compared to the number of people afflicted by the disease.

The fundamental cause of SCD is the decreased deformability of the sickled RBCs produced by gelation of hemoglobin S molecules during de-oxygenation. The deformation of sickle red cells upon complete de-oxygenation is due to the intracellular HbS polymerization. The gelation or polymerization is initiated by nucleation of a single polymer. Two types of HbS nucleation (i.e., homogeneous and heterogeneous) have been observed. The nucleation is due to the aggregation of hemoglobin S molecules. Once a certain size or the critical nucleus is reached, other monomers of HbS add endlessly to form a very large polymer. Then due the heterogeneous nucleation polymers are formed on the surface of the pre-existing polymer. Individual polymer is a fiber which is made up of 14 inter-wined helical strands of HbS molecules of seven inter-wined double strands. In each molecule, one of the two β6 Valines of the α2 β2 tetramer is involved in an intermolecular contact with its neighbor in the double strand (Report by the Secretariat, 117th session of Executive Board (EB117/34) Geneva: World Health Organization; 2005, WHO, Sickle cell anemia; p. 1).

Oxidative stress may contribute to the sickling process with formation of dense cells, development of vasoocciusion and shortened RBC survival. Oxidative damage in sickle RBC is most likely the consequence of the inherent instability of hemoglobin S, which results in a concomitant increase in free radical generation in association with impaired antioxidant defense (Lachant N A, Tanaka K R., Antioxidants in sickle cell disease: The in vitro effects of ascorbic acid, Am J Med Sci. 1986; 292:3-10).

Peripheral blood smears of subjects with steady sickle cell disease (SCD) with controls by counting ten 100× microscope fields were used to calculate percent of irreversible and reversible SC from total red cell population SC index (SCI). Controls had a small SCI. Children with hemoglobin SS had a significantly higher SCI. SCI increased with each increasing year and patients with higher SCI are likely to experience clinical complications (Alvarez O, Montague N S, Marin M, O'Brien R, Rodriguez M M, Quantification of Sickle Cells in the Peripheral Smear as a Marker of Disease Severity, Fetal Pediatr Pathol. 2015 June; 34(3):149-54). Although blood transfusions and hydroxyurea slightly decreased SCI, 72% treated patients still had high SCI, correlating with persistent sickling (Alvarez O, Montague N S, Mann M, O'Brien R, Rodriguez M M, Quantification of Sickle Cells in the Peripheral Smear as a Marker of Disease Severity, Fetal Pediatr Pathol. 2015 June; 34(3):149-54). In conclusion, transfusion and/or hydroxyurea have little impact on SCI, highlighting a need for a more effective anti-sickling strategy.

BRIEF SUMMARY

The present invention provides a nano-composition comprising nanoparticles, a method of forming the nano-composition, and a method of using the composition. The nanoparticles comprise a polycationic polymer ionically bonded to one or more polyanionic Glycosaminoglycans (GAGs), wherein the polycationic polymer is selected from the group consisting of chitosan, methylated chitosan, poly L-Lysine, and poly L-Arginine.

BRIEF DESCRIPTION OF THE DRAWINGS

FIG. 17 illustrates the potent anti-sickling effect of SNACH in preventing and reversing sickling of RBC from SCD subjects when subjected to hypoxia for 2-4 hours at 25 degree centigrade, in accordance with embodiments of the present invention.

FIG. 20 depicts individual patients' post-acute crisis (patient #2) illustrating the potent anti-sickling effect of SNACH in preventing and reversing sickling of RBC from SCD subjects when subjected to hypoxia for 2-4 hours at 25 degree centigrade, in accordance with embodiments of the present invention.

FIG. 21 depicts individual patients' (patient #3) illustrating the potent anti-sickling effect of SNACH in preventing and reversing sickling of RBC from SCD subjects when subjected to hypoxia for 2-4 hours at 25 degree centigrade, in accordance with embodiments of the present invention.

FIG. 22 depicts individual patients' with once a month acute crisis (Patient #4) illustrating the potent anti-sickling effect of SNACH in preventing and reversing sickling of RBC from SCD subjects when subjected to hypoxia for 2-4 hours at 25 degree centigrade, in accordance with embodiments of the present invention.

FIG. 27 depicts a representative illustration for the effect of SNACH on RBC from healthy subjects showing no effect on the normal morphology of RBC obtained from normal subjects, in accordance with embodiments of the present invention.

DETAILED DESCRIPTION

Figure 1:
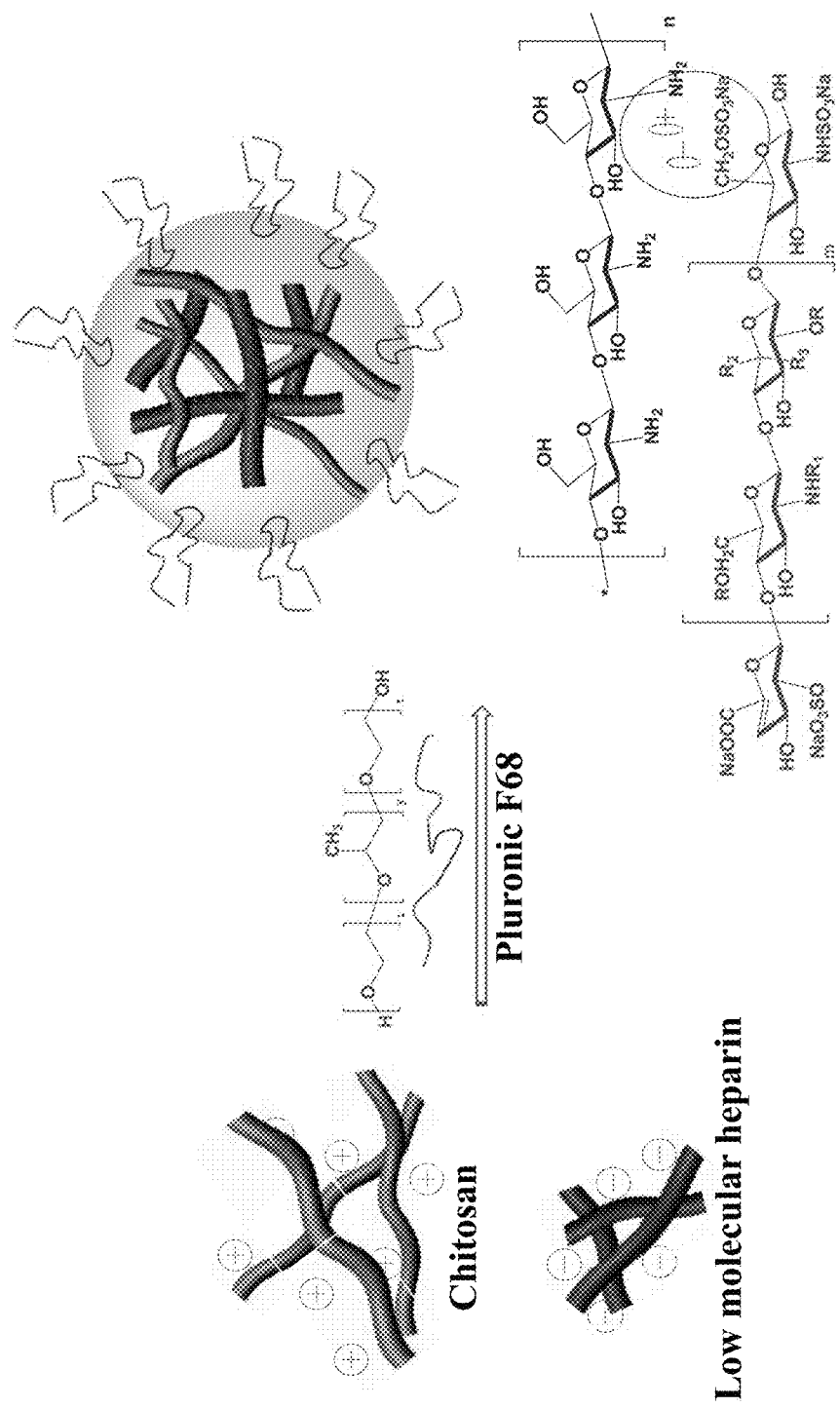
FIG. 1 depicts preparation of chitosan (average Molecular Weight 5,000-100,000 Daltons)+Low Molecular Weight Heparin (average Molecular Weight 4,000-8,000 Daltons; example Tinzaparin) nanoparticles (NPs), in accordance with embodiments of the present invention.

A series of novel glycosaminoglycans (GAGs) such as, inter alia, Sulfated Non-Anticoagulant Heparin (SNACH) derivatives, sulfated oligosaccharides, dermatan sulfate, heparin sulfate, sulfated Low Molecular Weight Heparins (LMWH), heparan sulfate, chondroitin sulfate, and fucoidan Nanoformulated for oral, topical, and injectable delivery were shown to have very effective anti-sickling effects via: (a) increased the oxygen affinity of sickle hemoglobin; and (b) inhibited in vitro hypoxia-induced sickling of red blood cells obtained from patients with sickle cell disease without causing hemolysis.

Combinations of selected GAGs, such as SNACH derivatives and linear and branched sulfated oligosaccharides, demonstrated additives to synergistic anti-sickling effects. Additionally, additive to synergistic anti-sickling effect was demonstrated between GAGs such as SNACH derivatives alone or co-encapsulated with the heterocyclic aldehyde 5-hydroxymethyl-2-furfural (5-HMF), L-Carnitine derivatives (L-propionyl carnitine), L-Glutamine, derivatives (Sodium thiosalicylate, ethyl thiosalicylate, . . . ) and/or L-Arginine and Zinc in increasing oxygen affinity, decreasing HbS polymerization, dehydration, and in decreasing RBC sickling during hypoxia. Co-encapsulated with X means encapsulated within a shell comprising X.

The formation of irreversibly sickled cells induced by 2-24 hours incubation of sickle-cell anemia erythrocytes under 95% N2/5% CO2 mixture is significantly decreased in the presence of high concentration of SNACH. These in-vitro 2-24 hours hypoxia studies showed that L-propionyl carnitine and/or aldehyde 5-hydroxymethyl-2-furfural (5-HMF) in combination with SNACH, GAGs, is beneficial in maintaining the normal shape of sickle-cell anemia erythrocytes at low oxygen tension.

Reversal of sickling was demonstrated using combinations of selected GAGs such as SNACH derivatives alone or co-encapsulated with polyphenols: flavone, isoflavones, flavonoids (Example: ellagic acid, punicagilin, catchins, resveratrol, nigella sativa extract derived thymoquinones, crucumin and others) and/or natural thiol containing compounds (Example: thiosalicylic acid, glutathione, garlic extract derived compounds as well as ion transport inhibitors such as disodium cromoglycate, o-vanillin, or combinations thereof.

Prevention and reversal of sickling was demonstrated using combinations of selected GAGs such as SNACH derivatives alone or co-encapsulated with sphingosine-1-phosphate modulators (S1P), antagonists, S1P inhibitors, or combinations thereof.

Formulations and Route of Administration

The present invention provides oral, injectable, and topical nanoformulations of GAGs such as Sulfated Non-Anticoagulant Heparin (SNACH) derivatives, sulfated oligosaccharides, dermatan sulfate, heparin sulfate, sulfated Low Molecular Weight Heparins (LMWH), heparan sulfate, chondroitin sulfate, and fucoidan alone or co-encapsulated with polyphenol, thiols, amino acids, thymoquinone, L-propionyl carnitine, disodium cromoglycate, o-vanillin, or combinations thereof.

Several polyanionic GAGs such as LMWH are approved for the prevention and treatment of thromboembolic disorders but are associated with bleeding. Hence, the present invention provides novel sulfated non-anticoagulant LMWH (SNACH) that are devoid of systemic anticoagulant activity but maintain all other pharmacological properties of heparin and can be dosed safely at higher doses to realize the full potential of heparins.

Chitosan oligosaccharide (CO) and/or Poly L-Lysine (PL) are polymers with a high net positive charge (polycationic) and may be transported across the intestine to deliver drugs into the blood occurs as discrete nanoparticles. Chitosan nanoparticles are tightly packed and highly dense CO with ionic crosslinks. LMWH cross-link chitosan and the novel nanoparticle (CO-LMWH) along with different stabilizers (a non-ionic surface coating of pluronic (F-68)) provided unique nanoformulations for oral delivery. Furthermore for sustained release and prolonged half-life, covalent bonding was carried on the ionically formed CO-LMWH nanoparticles by adding EDC, (N-(3-Dimethylaminopropyl)-N'-ethylcarbodiimide hydrochloride) and 1 to 10% (e.g., 5%) mannitol or sucrose was added as a cryprotectant prior to lyophilization.

Data in conjunction with the present invention indicates the effective release of LMWH from CO-LMWH in vitro (APTT) and in vivo (mouse studies). Three nanoparticles synthesized were CO-LMWH1, CO-LMWH2, and CO-LMWH3. CO-LMWH1 lacks F-68 coat. CO-LMWH2 has a F-68 coat with a ratio of CO to LMWH of about 1:1. CO-LMWH3 has a F-68 coat with ratios of CO to LMWH of 3:1. All three Nanoformulations were subjected to EDC for covalent bond formation in order to achieve slow and sustained release kinetics for LMWH and other GAGs. Nanoparticles were determined to be about 150-500 nm in diameter using dynamic light scattering (DLS). The surface potentials of CO-LMWH2 and CO-LMWH3 were −46 mV and +30 mV respectively.

Nanoformulations

The mean particle size of the GAGs such as Sulfated Non-Anticoagulant Heparin (SNACH) Derivatives, glycosaminoglycans (GAGs), and sulfated oligosaccharides, dermatan sulfate, heparin sulfate, sulfated Low Molecular Weight Heparins (LMWH), heparan sulfate, chondroitin sulfate, and fucoidan) with optima loading ranged from 150-500 nm. All evaluation data, using infrared spectroscopy, Raman spectroscopy, powder X-ray diffractometry, differential thermal analysis and scanning electron microscopy, confirmed the successful formation of the inclusion complex of GAGs with the nano-carrier platforms utilized for the present invention.

The present invention uses GAGs such as Sulfated Non-Anticoagulant Heparin (SNACH) Derivatives, sulfated oligosaccharides, dermatan sulfate, heparin sulfate, sulfated Low Molecular Weight Heparins (LMWH), heparan sulfate, chondroitin sulfate, and fucoidan alone or co-encapsulated with polyphenol, thiols, amino acids, thymoquinone, L-propionyl carnitine, disodium cromoglycate, o-vanillin, or combinations thereof.

A. Chitosan Cross Linked to Various Acids:

Chitosan or trimethylated chitosan hydrogels cross-linked with alginic acid and with hyaluronic acid were prepared by freeze-drying and have been studied for topical use. The effect of the nature of the cross-linker on GAG permeation through porcine skin and the main permeation parameters (diffusion coefficient, flux and lag time) was calculated. All the chitosan hydrogels encapsulating GAG were analyzed for oral and transcutaneous permeation as compared to the corresponding solution of the GAG. The interaction of the hydrogels with the stratum corneum in increasing the solubility of the GAG in the skin were evaluated.

Co-Polymer Complex Encapsulating Various GAGs

A surface modification of (i) NIPAAM-APMAH-AA nanoparticles with excess APMAH results in a positive surface charge of the shell of the NIPAAM-APMAH-AA nanoparticles; (ii) no surface modification of NIPAAM-APMAH-AA nanoparticles results in a negative surface charge of the shell of the NIPAAM-APMAH-AA nanoparticles, and (iii) a surface modification of nanoparticles with surfactant such as a Tween® 80 coating results in the shell of the nanoparticles being electrically neutral, wherein NIPAAM is N-isopropyl acrylamide, APMAH is N-3-aminopropylmethacrylamide hydrochloride, and AA is acrylic acid to be positive.

Solid Nanoparticles (SLN)

Topical and oral application of GAGs using nanoparticulate carrier system like nanostructured lipid carriers (NLCs) should improve skin penetration of GAGs. GAG-loaded NLCs were prepared by the solvent diffusion technique. The effect of formulation and process variables on the physicochemical properties of prepared NLCs were studied and characterized. In vitro skin permeation studies compared the penetration of GAGs by NLCs as compared to plain GAGs. The in vivo skin retention, skin irritation and consequently the effectiveness of particulate system as a vehicle for topical delivery of GAGs were evaluated in pigs.

Permeation Enhancers

The highly organized structure of the stratum corneum provides an effective barrier to the drug delivery into or across the skin. To overcome this barrier function, penetration enhancers (e.g., caproic acid) were evaluated in the transdermal and dermal drug delivery systems without causing irritation.

Alginate-Hyaluronic Acid Cross Linked Chitosan Core Shell Nanoparticles for Oral Delivery of GAGs Alginate-Hyaluronic acid cross linked chitosan NPs resulted in 20-40% oral bioavailability of SNACH, LMWH, and other GAGs

Example 1: Preparation of Nanoparticles

In a typical experiment, 30 mL of a solution of the LMWH Tinzaparin or SNACH (2 mg/mL in deionized water) was added drop by drop to 50 mL of 2 mg/mL chitosan or methylated Chitosan (Example 2) solution with constant ultrasonic. Then pluronic F-68 (1% W/V) was added mixed by shaking and followed by being homogenized for 30 seconds using ultrasound sonication (200 W) (Table 1). Ionically formed Nanoparticles are then further covalently bonded using EDC for sustained and extended release of LMWH or SNACH (see FIGS. 1-6).

Example 2: Synthesis of Tri-Methylated TMC from Chitosan 200 mg of chitosan and 0.48 g of sodium iodide were added to a mixture of 10 ml of NMP (N-Methyl-2-pyrrolidone) and 1.2 ml of 15% w/v aqueous NaOH solution. Subsequently, the mixture was heated to 60° C. and after stirring for 20 min, 0.6 ml of methyl iodide was added and the reaction mixture was refluxed for 60 min. To synthesize TMC with a DQ of around 40-50%, 0.6 ml of 15% NaOH solution and 0.3 ml of iodomethane were added and the solution was stirred for another 60 min before stopping the reaction.

TABLE 1

Nano composite of Ionic complex of the LMWH Tinzaparin and Chitosan Nanoparticles

| Components | Ratio (mg) | Particle Sizes (nm ± SD) | PDI | Zeta Potential (mv ± SD) |
|---|---|---|---|---|
| Chitosan-10k/Tinzaparin (F-68 1%) | 1:0.38 | 148 | 0.18 | +32.9 ± 2.6 |
| Chitosan-10k/Tinzaparin (F-68 1%) | 1:0.6 | 214 | 0.14 | +30.2 ± 2.6 |
| Chitosan-10KD/Tinzaparin (F-68 1%) | 1:1 | 214 | 0.11 | +21.2 ± 1.7 |
| Chitosan-10KD/Tinzaparin (F-68 1%) | 1:1.05 | 263 | 0.15 | +19 ± 1.5 |
| Chitosan-10KD/Tinzaparin (F-68 1%) | 1:1.1 | 474 | 0.18 | +12.3 ± 0.9 |
| (unstable) Aggregation after one day | | | | |
| Chitosan-10KD/Tinzaparin (F-68 1%) | 1:1.2 | Aggregation | | |
| Chitosan-10KD/Tinzaparin (F-68 1%) | 1:1.4 | Aggregation | | |
| Chitosan-10KD/Tinzaparin (F-68 1%) | 1:1.5 | 218 | 0.15 | −20.4 ± 1.9 |
| Chitosan-10KD/Tinzaparin (F-68 1%) | 1:2 | 234 | 0.14 | −24.4 ± 1.9 |
| Chitosan-10KD/Tinzaparin (F-68 1%) | 1:3 | 223 | 0.18 | −27.4 ± 2.1 |
| Chitosan-10KD/Tinzaparin (F-68 1%) | 1:4 | 187 | 0.14 | −27.5 ± 2.1 |

In Table 1, the Chitosan or Methylated Chitosan Molecular Weight ranges from 5-50 K Dalton.

Example 3: Freeze-Drying of Nanoparticles

Mannitol (5% W/V) was added to the solution as a cryprotectant to preserve the particle properties during freezing step. Then the solution was then lyophilized to get the nanoformulation in powdered form for further use (see Table 2)

TABLE 2

Freeze-drying of the LMWH Tinzaparin/Chitosan or Methylated Chitosan nanoparticles

| Components | Ratio (mg) | After freeze-drying Particle size (nm ± SD) | PDI | Zeta Potential (mv ± SD) |
|---|---|---|---|---|
| Chitosan-10 KD/Tinzaparin (F-68 1%) + 5% Mannitol | 1:0.38 | 256 | 0.17 | +30.6 ± 2.4 |
| Chitosan-10 KD/Tinzaparin (F-68 1%) + 5% Mannitol | 1:0.6 | 311 | 0.20 | +23.1 ± 1.8 |
| Chitosan-10 KD/Tinzaparin (F-68 1%) + 5% Mannitol | 1:1.4 | 299 | 0.11 | −21.7 ± 1.7 |
| Chitosan-10 KD/Tinzaparin (F-68 1%) + 5% Mannitol | 1:1.6 | 282 | 0.14 | −23.8 ± 1.9 |
| Chitosan-10 KD/Tinzaparin (F-68 1%) + 5% Mannitol | 1:2 | 315 | 0.15 | −29.0 ± 2.3 |
| Chitosan-10 KD/Tinzaparin (F-68 1%) + 5% Mannitol | 1:3 | 302 | 0.13 | −30.7 ± 2.4 |

Example 4: Encapsulation and Freeze Drying of Ionically and/or Covalently Complexed SNACH/Chitosan or Methylated Chitosan The protocol is as under examples 1-3. Table 3A and Table 3B illustrate the data generated.

TABLE 3A

Encapsulation of S-NACH into Chitosan Nanoparticles

| Components | Ratio (mg) | Particle Sizes (nm ± SD) | PDI | Zeta Potential (mv ± SD) |
|---|---|---|---|---|
| Chitosan-10KD/S-NACH (F-68 1%) | 1:0.3 | 201 | 0.10 | +34.9 ± 2.7 |
| Chitosan-10KD/S-NACH (F-68 1%) | 1:1.5 | 230 | 0.15 | −26.4 ± 2.0 |

TABLE 3B

Freeze-drying of S-NACH/Chitosan Nanoparticles

| Components | Ratio (mg) | Particle Sizes (nm ± SD) | PDI | Zeta Potential (mv ± SD) |
|---|---|---|---|---|
| Chitosan-10KD/S-NACH (F-68 1%) + 5% Mannitol | 1:0.3 | 190 | 0.11 | +35.0 ± 3.2 |
| Chitosan-10KD/S-NACH (F-68 1%) + 5% Mannitol | 1:1.5 | 220 | 0.13 | −25.0 ± 2.5 |

Example 5: Thrombelastography (TEG)

Testing SNACH in the standard platelet/fibrin clot dynamic and kinetic system TEG was carried out versus 5-HMF, L-Glutamine, and Thymoquinone in blood obtained from healthy and sickle cell subjects.

Figure 7:
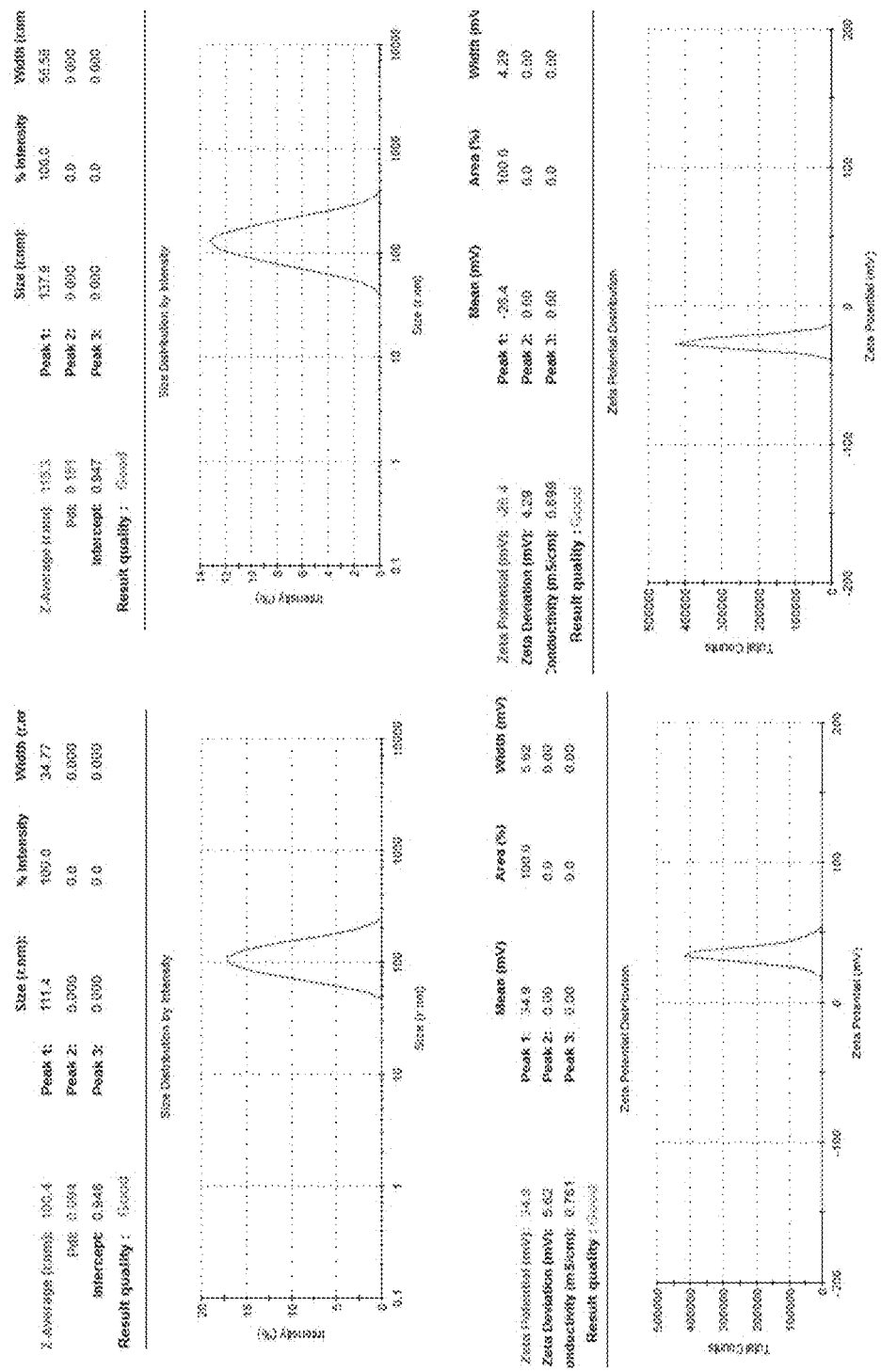
FIG. 7 pertains to encapsulation of S-NACH into Chitosan Nanoparticles, in accordance with embodiments of the present invention.

Blood Sampling: Siliconized Vacutainer tubes (Becton Dickinson, Rutherford, N.J.) were used to collect whole blood from healthy volunteer versus sickle cell subject. To maintain a ratio of citrate to whole blood of 1:9 (v/v), the tubes contained 3.2% sodium citrate. Blood samples were placed on a slow speed rocker until TEG analysis. FIG. 7 shows representative TEG tracings and clot kinetic parameters.

Example 6: TEG Clot Kinetic of SCD Subjects Versus Healthy Subjects

Figure 8:
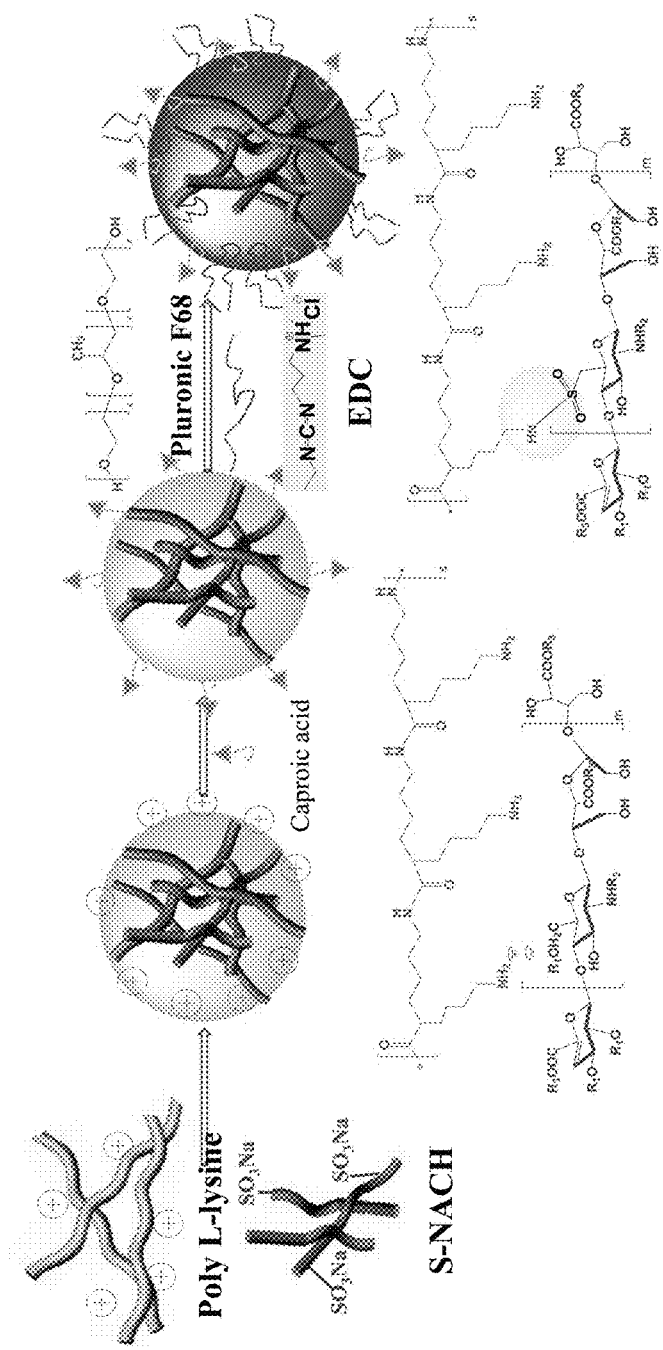
FIG. 8 depicts preparation of poly L-lysine/S-NACH nanoparticles through the combination of two components with opposite charges (inserts middle down showing the chemical structure of poly L-lysine with positive charge and S-NACH with negative charge), followed by coating with caproic acid and pluronic F-68 to form a shell, in accordance with embodiments of the present invention.

Thrombelastography (TEG): Whole Blood Coagulation Analyzer, Model 5000 Thrombelastography. TEG is based on the measurement of the physical viscoelastic characteristics of blood clots. An oscillating plastic cylindrical cuvette ("cup") and a coaxially suspended stationary piston ("pin") with a 1-mm clearance between the surfaces are used to monitor clot formation at 37° C. Every 4.5 seconds, with a 1-second mid cycle stationary period, the cup oscillates in either direction, resulting in a frequency of 0.1 Hz. A torsion wire that acts as a torque transducer suspends the pin. Fibrin fibrils link the cup to the pin during clot formation, and the rotation of the cup is transmitted to the pin via the viscoelasticity of the clot. Customized software and an IBM-compatible personal computer display the rotation. The pin's torque is plotted as a function of time, as shown by the different TEG clot parameters. FIG. 8 illustrate the differences in the clot kinetics between SCD and healthy subjects. Additionally, FIG. 9 tested the effects of SNACH in normalizing the abnormal clot kinetics in SCD subjects as opposed to other agents such as 5-HMF, L-Glutamine, and Thymoquinone.

Figure 10:
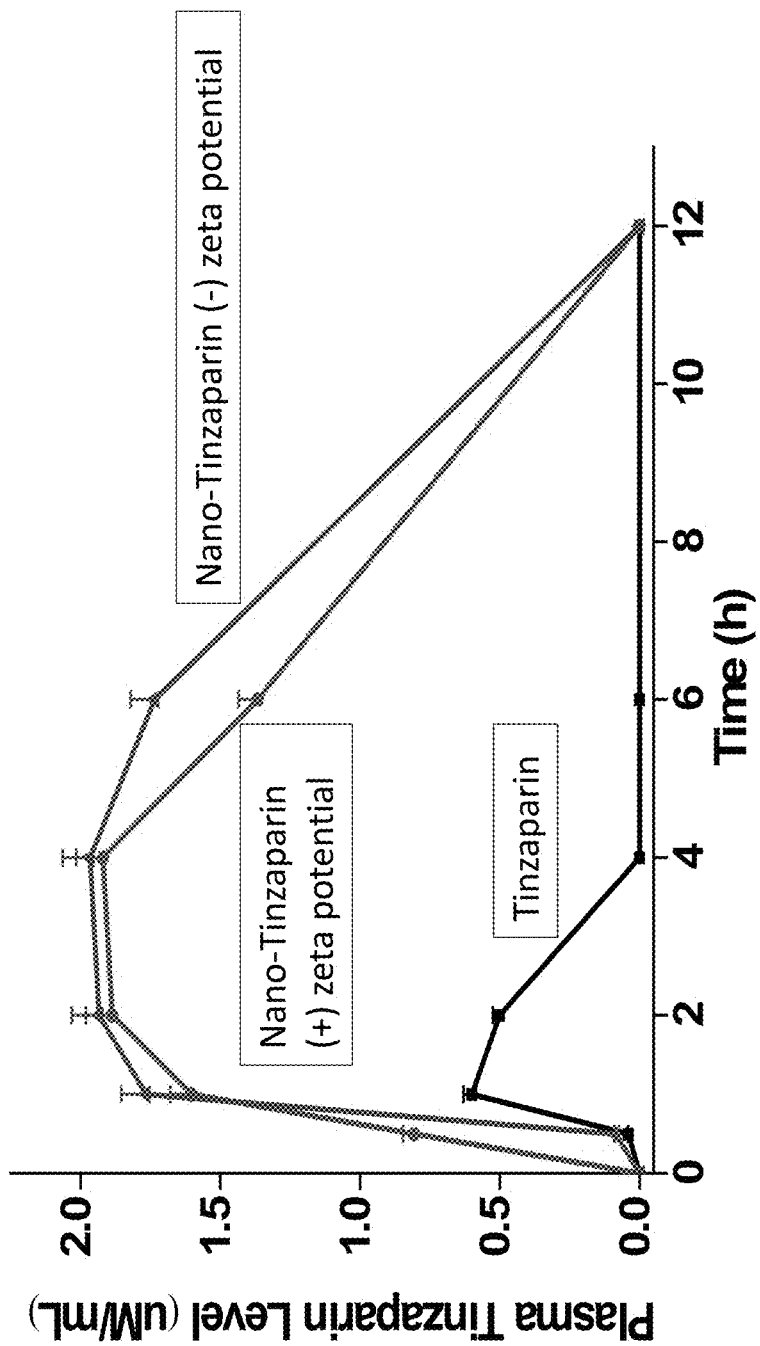
FIG. 10 is a graph of plasma tinzaparin level versus time profiles in mice with formulations administered by subcutaneous route into the mice at dose of 1.6 mg/kg, in accordance with embodiments of the present invention.

Example 7: In Vivo Pharmacokinetic (PK) of Nanoformulated LMWH Bioavailability after Subcutaneous Administration Versus Standard LMWH Nanoformulated LMWH as shown in earlier Examples 1-5 were administered subcutaneously to mice versus standard LMWH at the same dose. Blood samples were withdrawn at different time and plasma levels of LMWH were measured using colorimetric assay. FIG. 10 illustrate the distinct difference in the PK profiles for Nanoformulated LMWH tinzaparin (with either net positive or negative zeta potential) versus standard tinzaparin.

Figure 11:
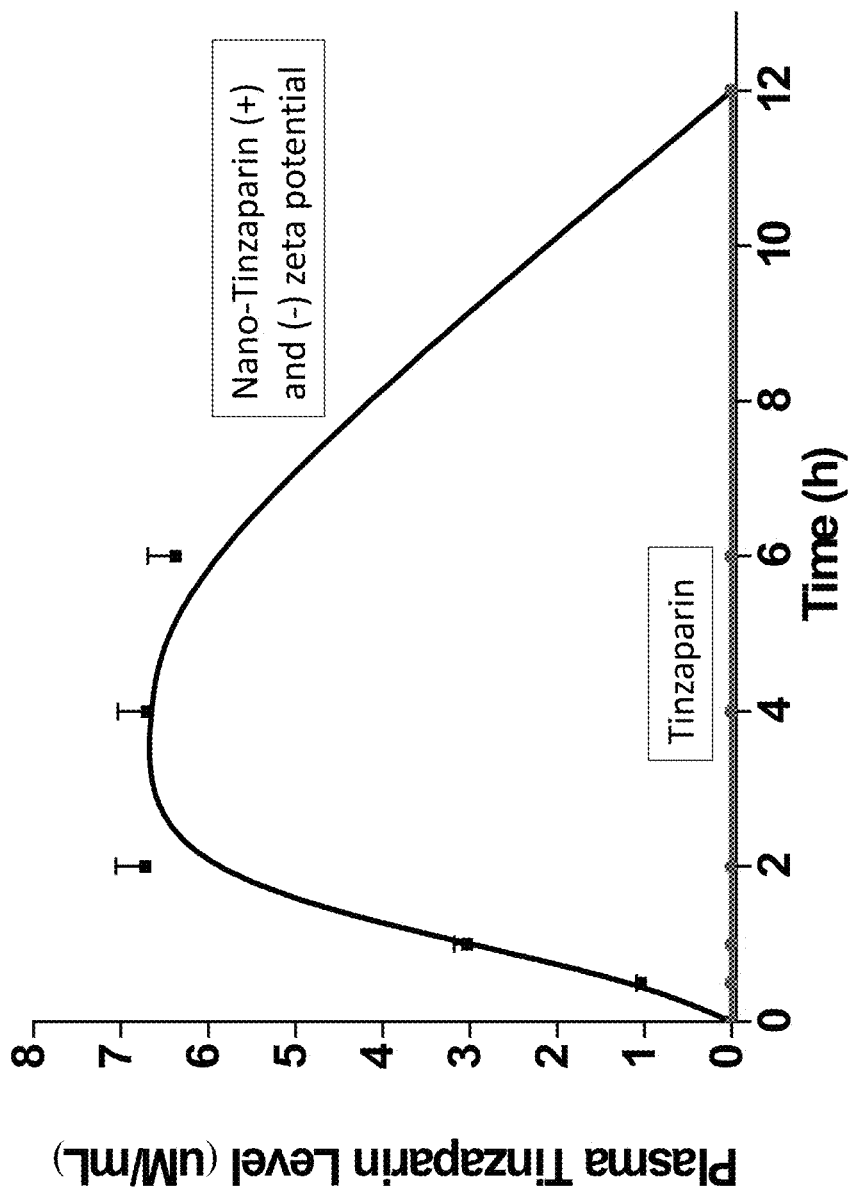
FIG. 11 is a graph of plasma tinzaparin level versus time profiles in mice with formulations administered by oral gavage into the mice at dose of 1.6 mg/kg, in accordance with embodiments of the present invention.

Example 8: In Vivo Pharmacokinetic (PK) of Nanoformulated LMWH Bioavailability after Oral Administration Versus Standard LMWH Nanoformulated LMWH as shown in Examples 1-5 were administered orally to mice versus standard LMWH at the same dose. Blood samples were withdrawn at different time and plasma levels of LMWH were measured using colorimetric assay. FIG. 11 illustrates the distinct difference in the PK profiles for Nanoformulated LMWH tinzaparin versus standard tinzaparin, which have no detectable blood levels.

Example 9

Red Blood Cell (RBC) sickling were studied in blood samples obtained from 12 sickle cell subjects and 6 samples from healthy volunteers matched in terms of age and gender. The blood samples from the subjects were withdrawn and mixed into EDTA tube (10 ml), and then divided into 2 tubes 4-5 ml each (One containing S-NACH 10-100 ug/ml blood added at 10 ul/1 ml blood or PBS buffer solution).

Figure 12:
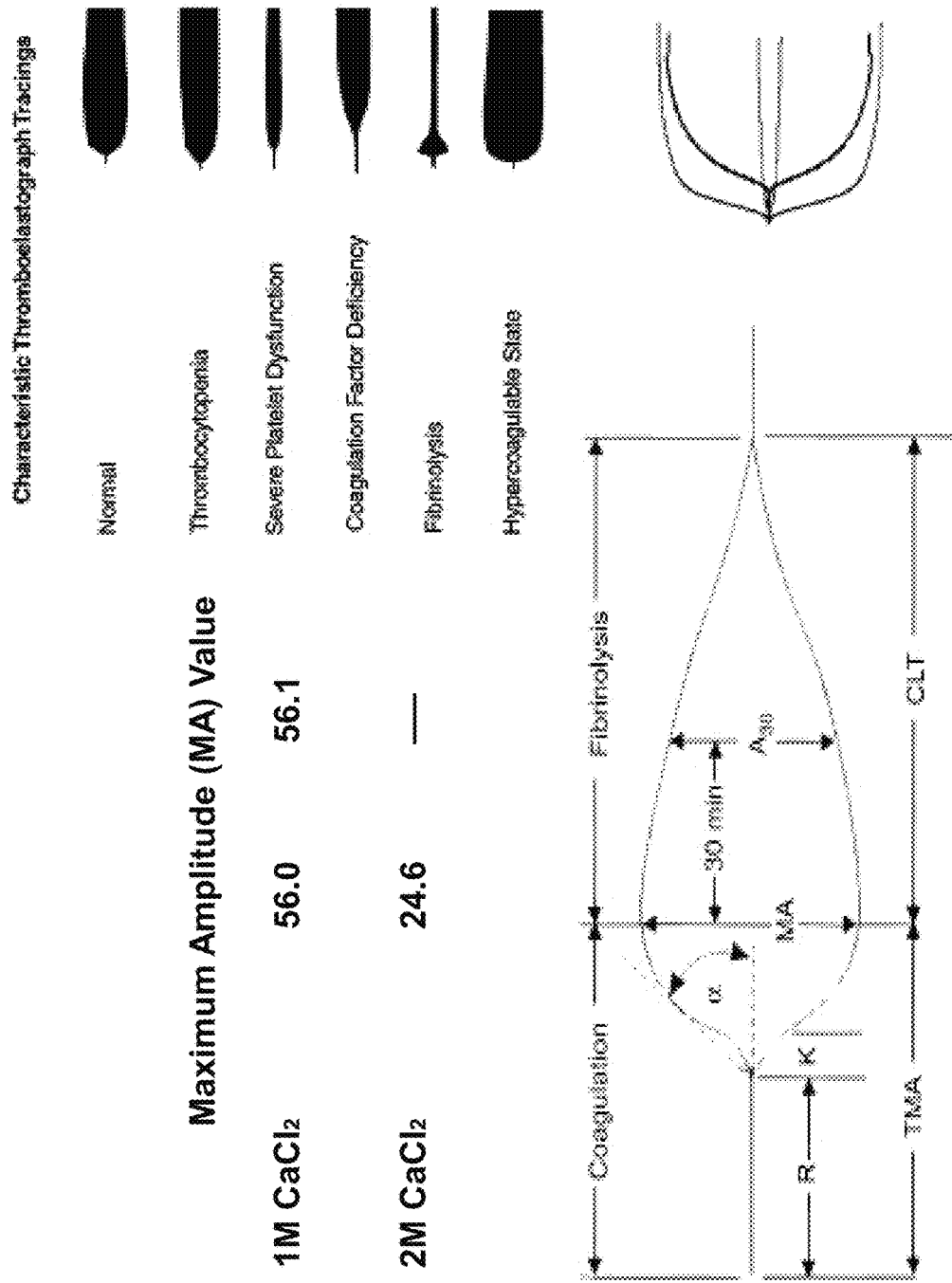
FIG. 12 depicts a representative Thrombelastograph for human blood clot kinetic parameters; in accordance with embodiments of the present invention.

FIG. 12 shows representative blood film for sickle RBC.

Example 10

Blood samples were incubated for 2-3 hours at room temperature and then blood smears were obtained for monitoring shape of RBCs (take photos for later quantitation number of normal vs. sickle RBCs). Then blood samples were centrifuged to get the plasma, and the plasma were frozen for further testing of various biomarkers.

FIGS. 13-26 illustrate the effective anti-sickling for SNACH in all SCD subjects without any effect on normal RBC from healthy subjects.

FIG. 1 depicts preparation of chitosan (average Molecular Weight 5,000-100,000 Daltons)+Low Molecular Weight Heparin (average Molecular Weight 4,000-8,000 Daltons; example Tinzaparin) nanoparticles (NPs), in accordance with embodiments of the present invention. The two components being combined have opposite charges (inserts right down showing the chemical structure of chitosan with positive charge and Tinzaparin with negative charge), which is followed by coating with pluronic F-68 to form a shell of a nanoparticle. The prepared NPs can prevent the release of tinzaparin from CS NPs in the stomach and enhance their absorption on the surface of the small intestine, and PEG coating NPs would increase stability in gastric and biological fluids, which can prolong the NPs' circulation and retard elimination, thus further increasing their bioavailability. The resultant ionically linked Nanoparticles have a size ranged from 150-500 nm. Before lyophilization, 5% mannitol or sucrose were added as a cryoprotectant.

Figure 2:
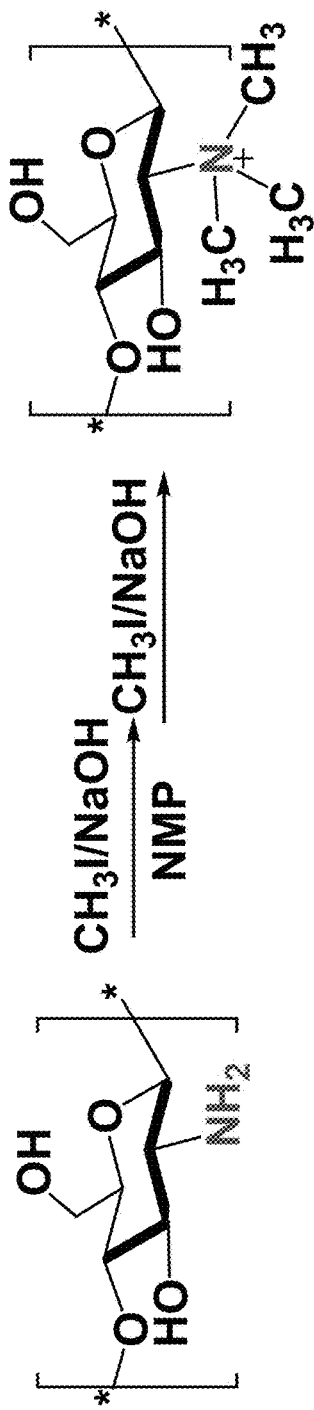
FIG. 2 depicts synthesis of O-methylated TMC (N,N,N-trimethylated chitosan) from chitosan, in accordance with embodiments of the present invention.

FIG. 2 depicts synthesis of O-methylated TMC (N,N,N-trimethylated chitosan) from chitosan, in accordance with embodiments of the present invention. 200 mg of chitosan and 0.48 g of sodium iodide were added to a mixture of 10 ml of NMP and 1.2 ml of 15% w/v aqueous NaOH solution. Subsequently, the mixture was heated to 60° C. and after stirring for 20 min, 0.6 ml of methyl iodide was added and the reaction mixture was refluxed for 60 min. To synthesize TMC with a DQ of around 40-50%, 0.6 ml of 15% NaOH solution and 0.3 ml of iodomethane were added and the solution was stirred for another 60 min before stopping the reaction. Product was characterized by MS and NMR.

Figure 3:
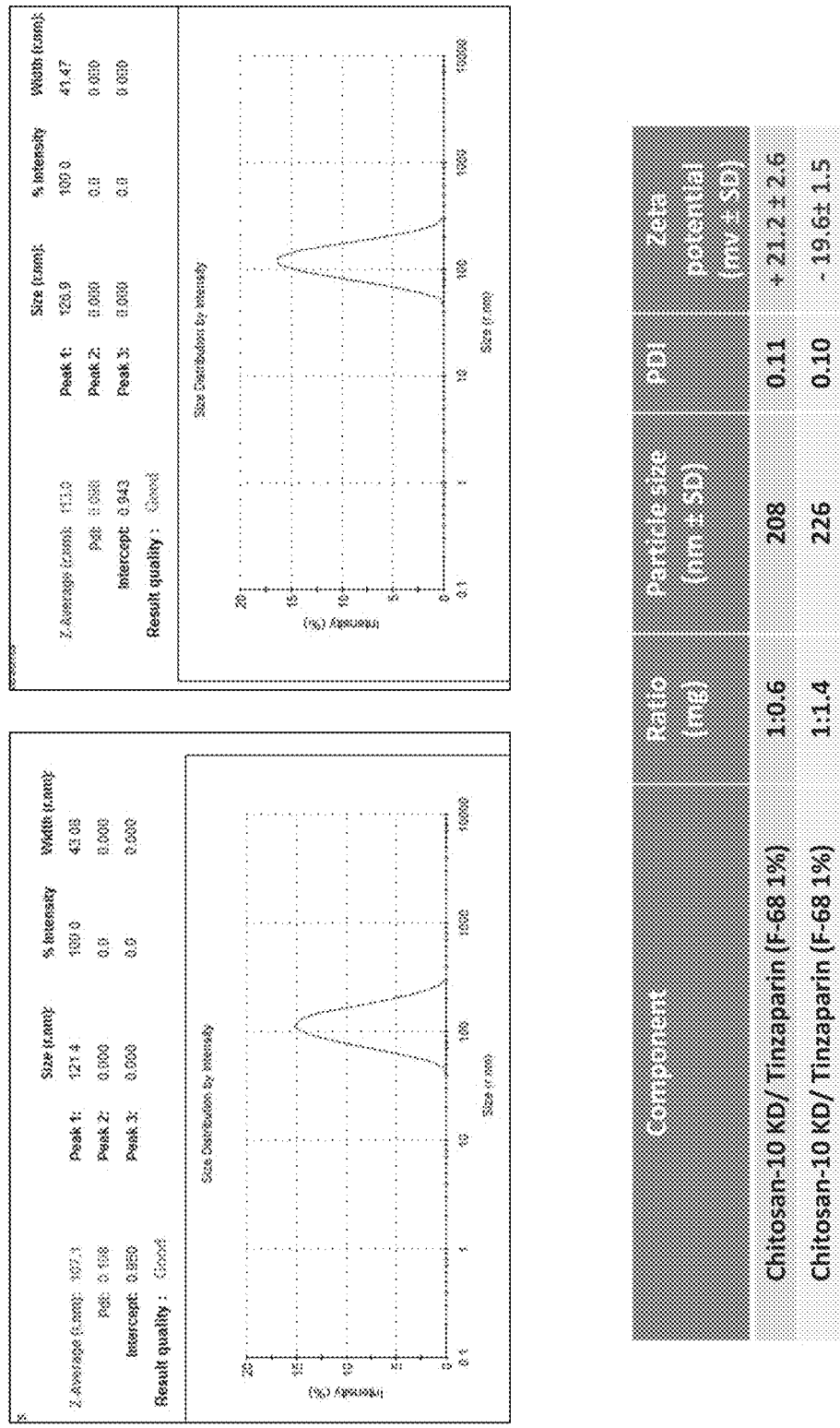
FIG. 3 pertains to encapsulation of 80 mg from the LMWH Tinzaparin into Chitosan nanoparticles, in accordance with embodiments of the present invention.

FIG. 3 pertains to encapsulation of 80 mg from the LMWH Tinzaparin into Chitosan nanoparticles, in accordance with embodiments of the present invention. In FIG. 3, there is an ionic complex of the LMWH tinzaparin with Chitosan or methylated Chitosan. Encapsulation of tinzaparin with chitosan along with the addition of 1% F-68 resulted in stable Nanoparticles with 120-127 nm size. Addition of EDC for covalent bonding and then 5% mannitol before lyophilization resulted in nanoparticle sizes ranging from 200-230 nm, with positive or negative zeta potential depending on the ratio of SNACH to Chitosan or methylated chitosan.

Figure 4:
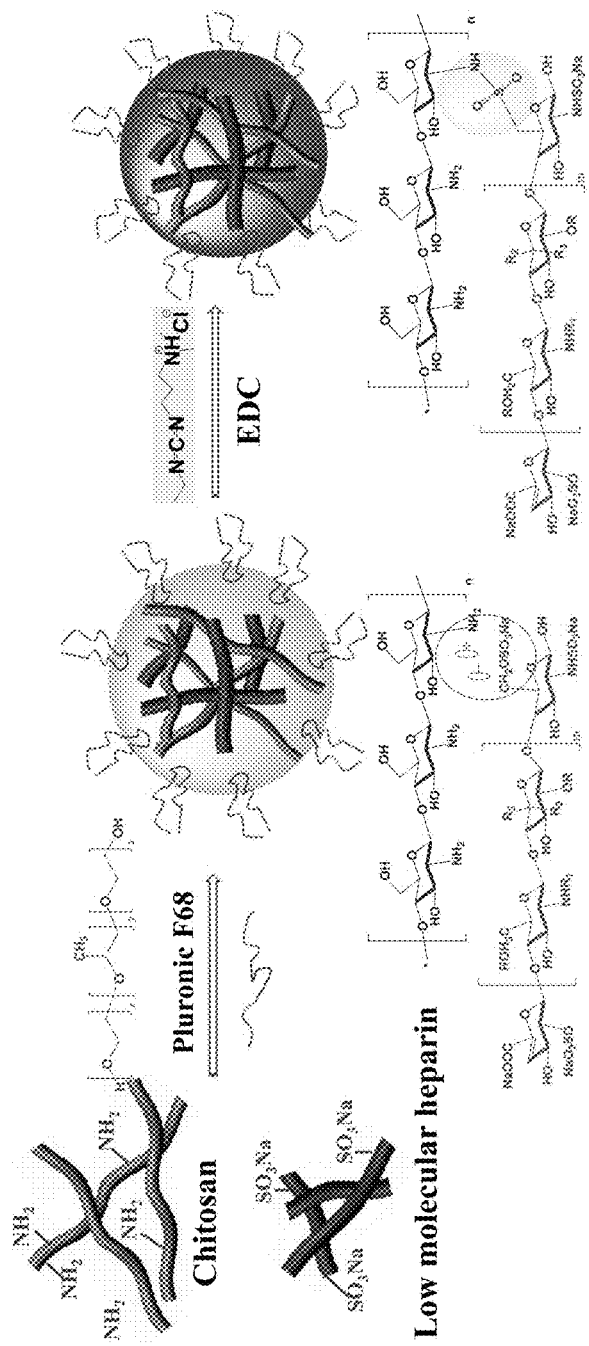
FIG. 4 depicts preparation of chitosan/Tinzaparin nanoparticles through the combination of two components with opposite charges (inserts middle down showing the chemical structure of chitosan with positive charge and Tinzaparin with negative charge), followed by coating with plutonic F-68 to form a shell, in accordance with embodiments of the present invention.

FIG. 4 depicts preparation of chitosan/Tinzaparin nanoparticles through the combination of two components with opposite charges (inserts middle down showing the chemical structure of chitosan with positive charge and Tinzaparin with negative charge), followed by coating with pluronic F-68 to form a shell, in accordance with embodiments of the present invention. Then the NPs were cross-linked with EDC (inserts right down showing the chemical structure of chitosan conjugated with Tinzaparin). The resultant ionically and covalently linked Nanoparticles have a size ranged from 150-500 nm. Before lyophilization, 5% mannitol or sucrose were added as a cryoprotectant.

Figure 5:
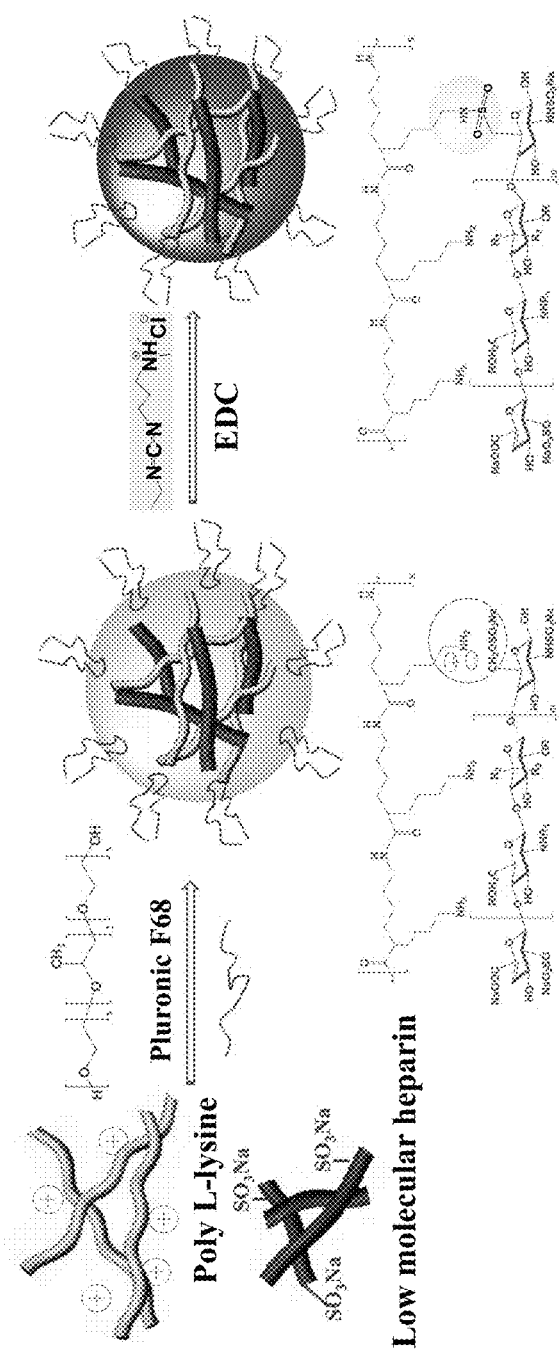
FIG. 5 depicts preparation of poly L-lysine/Tinzaparin nanoparticles through the combination of two components with opposite charges (inserts middle down showing the chemical structure of poly L-lysine with positive charge and Tinzaparin with negative charge), followed by coating with pluronic F-68 to form a shell; in accordance with embodiments of the present invention.

FIG. 5 depicts preparation of poly L-lysine/Tinzaparin nanoparticles through the combination of two components with opposite charges (inserts middle down showing the chemical structure of poly L-lysine with positive charge and Tinzaparin with negative charge), followed by coating with pluronic F-68 to form a shell, in accordance with embodiments of the present invention. Then the NPs were cross-linked with EDC (inserts right down showing the chemical structure of poly L-lysine conjugated with Tinzaparin). The resultant ionically linked Nanoparticles have a size ranged from 150-500 nm. Before lyophilization, 5% mannitol or sucrose were added as a cryoprotectant.

Figure 6:
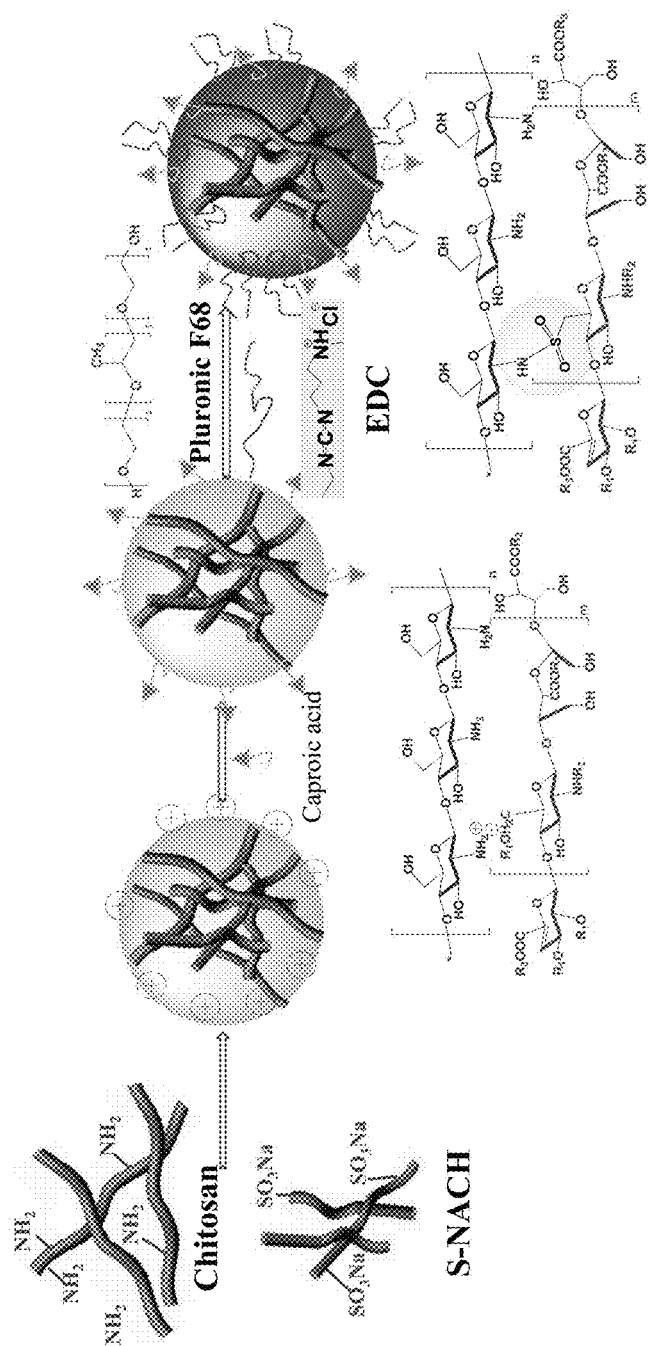
FIG. 6 depicts preparation of chitosan/S-NACH nanoparticles through the combination of two components with opposite charges (inserts middle down showing the chemical structure of chitosan with positive charge and S-NACH with negative charge), followed by coating with caproic acid and pluronic F-68 to form a shell, in accordance with embodiments of the present invention.

FIG. 6 depicts preparation of chitosan/S-NACH nanoparticles through the combination of two components with opposite charges (inserts middle down showing the chemical structure of chitosan with positive charge and S-NACH with negative charge), followed by coating with caproic acid and pluronic F-68 to form a shell, in accordance with embodiments of the present invention. Then the NPs were cross-linked with EDC (inserts right down showing the chemical structure of chitosan conjugated with S-NACH).

FIG. 7 pertains to encapsulation of S-NACH into Chitosan Nanoparticles, in accordance with embodiments of the present invention. In FIG. 7, there is an ionic complex of SNACH with Chitosan or methylated Chitosan. Encapsulation of tinzaparin with chitosan along with the addition of 1% F-68) resulted in stable Nanoparticles with 110-140 nm size, addition of EDC for covalent bonding and then 5% mannitol before lyophilization resulted in nanoparticle sizes ranging from 150-200 nm, with positive or negative zeta potential depending on the ratio of SNACH to Chitosan or methylated chitosan.

FIG. 8 depicts preparation of poly L-lysine/S-NACH nanoparticles through the combination of two components with opposite charges (inserts middle down showing the chemical structure of poly L-lysine with positive charge and S-NACH with negative charge), followed by coating with caproic acid and pluronic F-68 to form a shell, in accordance with embodiments of the present invention. Then the NPs were cross-linked with EDC (inserts right down showing the chemical structure of poly L-lysine conjugated with S-NACH). The resultant ionically and covalently linked Nanoparticles have a size ranged from 150-500 nm. Before lyophilization, 5% mannitol or sucrose were added as a cryoprotectant.

Figure 9:
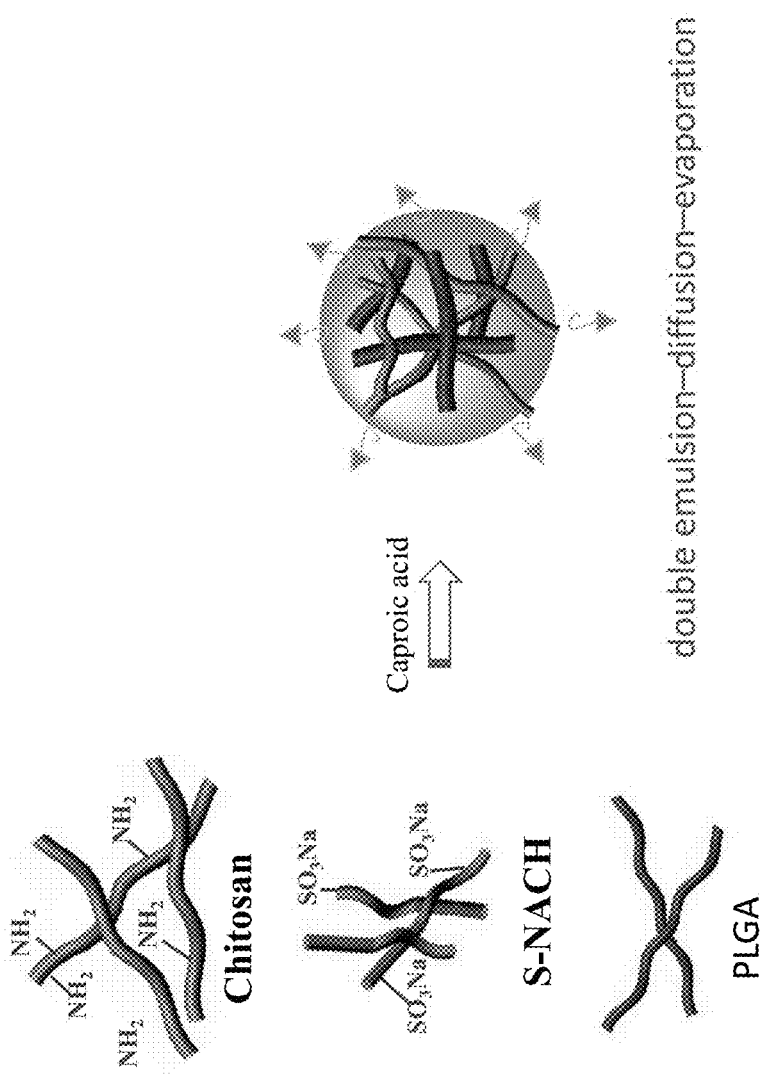
FIG. 9 depicts S-NACH containing nanoparticles prepared by double emulsion-diffusion-evaporation methods, in accordance with embodiments of the present invention.

FIG. 9 depicts S-NACH containing nanoparticles prepared by double emulsion-diffusion-evaporation methods, in accordance with embodiments of the present invention. The S-NACH is dissolved in water and emulsified with polymer in an organic phase that is then emulsified with the aqueous phase. After the solvent has evaporated, particles are washed and collected via centrifugation for lyophilization and long term storage.

FIG. 10 is a graph of plasma tinzaparin level versus time profiles in mice with formulations administered by subcutaneous route into the mice at dose of 1.6 mg/kg, in accordance with embodiments of the present invention. Graphs for Tinzaparin, Chitosan NPs with positive charge and Chitosan NPs with negative charge are shown. Data are shown as mean±SD (n=4).

FIG. 11 is a graph of plasma tinzaparin level versus time profiles in mice with formulations administered by oral gavage into the mice at dose of 1.6 mg/kg, in accordance with embodiments of the present invention. Graphs for Tinzaparin, and Chitosan NPs with positive charge and with negative charge are shown. Data are shown as mean±SD (n=4).

FIG. 12 depicts a representative Thrombelastography for human blood clot kinetic parameters, in accordance with embodiments of the present invention. The key parameters are: MA (mm) is the clot strength and R (minutes) is the lag time to clot generation.

Figure 13:
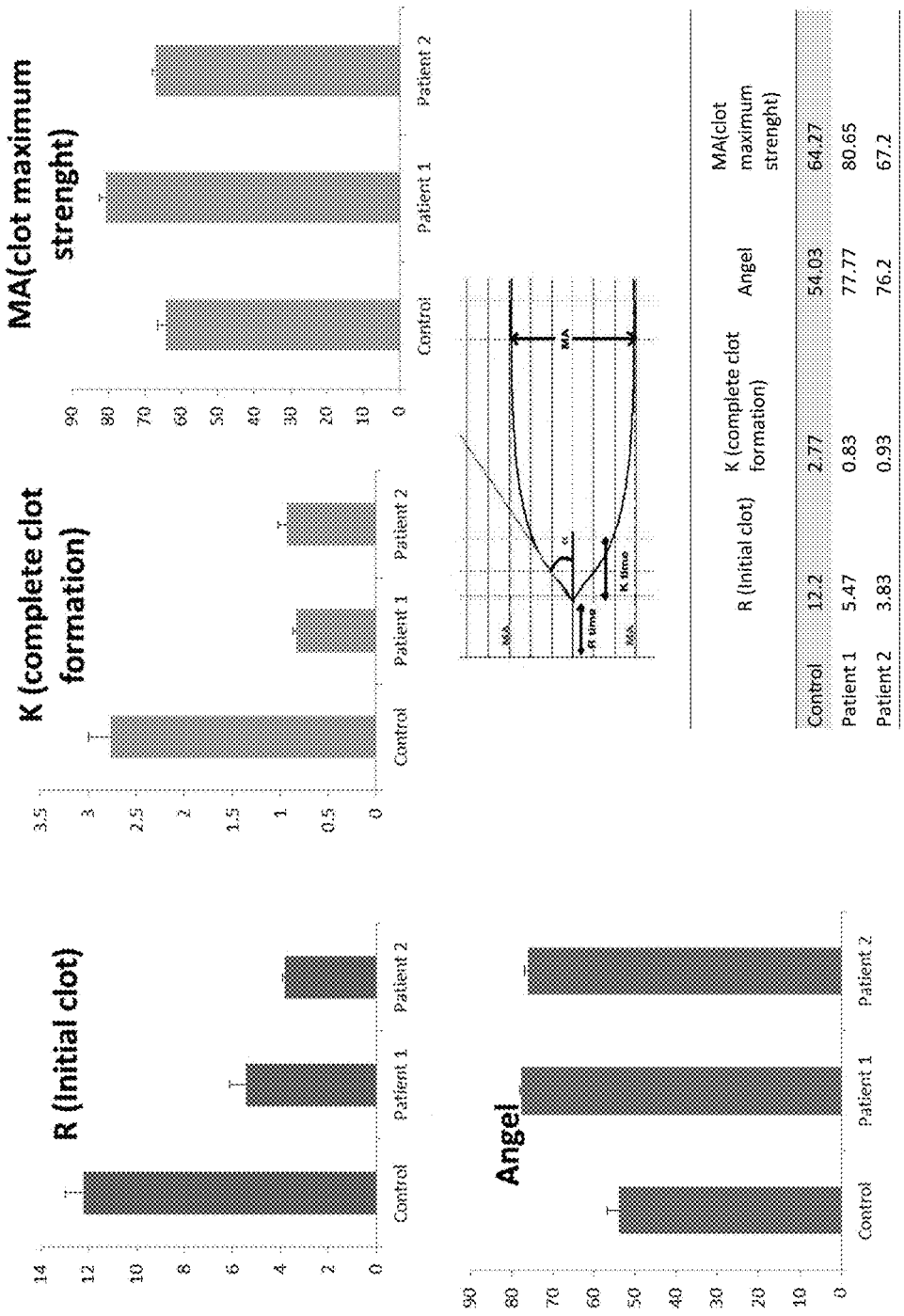
FIG. 13: depicts a representative Thrombelastograph for human blood clot kinetic parameters for analysis of sickle disease patients, in accordance with embodiments of the present invention.

FIG. 13: depicts a representative Thrombelastography for human blood clot kinetic parameters for analysis of sickle disease patients, in accordance with embodiments of the present invention. The key parameters for SCD subjects versus healthy subjects illustrate hyper-coaguability in SCD versus healthy subject.

Figure 14:
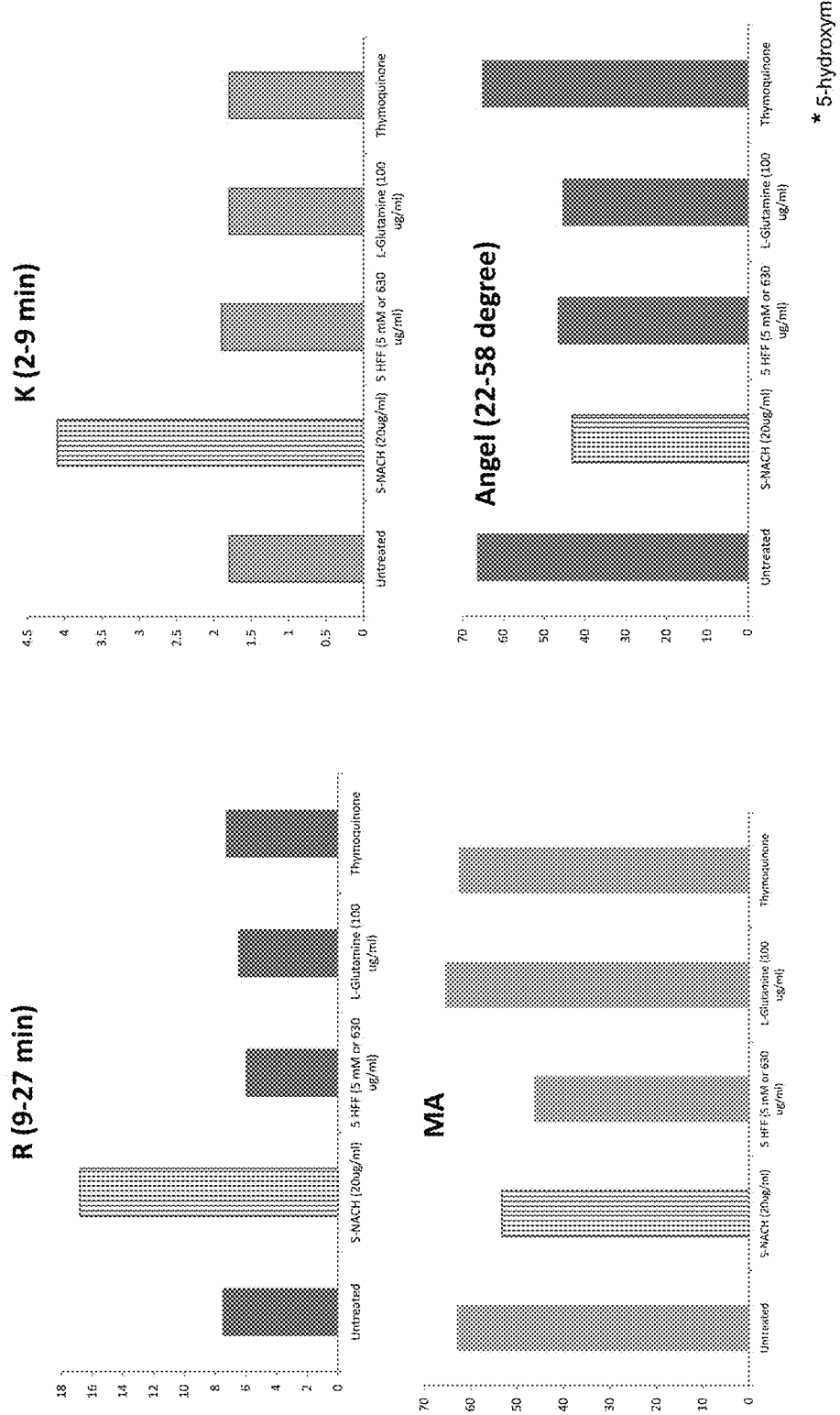
FIG. 14 depicts effect of SNACH, 5 HMF, L-Glutamine and Thymoquinone on clot kinetics in SCD subjects using TEG, in accordance with embodiments of the present invention.

FIG. 14 depicts effect of SNACH, 5 HMF, L-Glutamine and Thymoquinone on clot kinetics in SCD subjects using TEG, in accordance with embodiments of the present invention.

Figure 15:
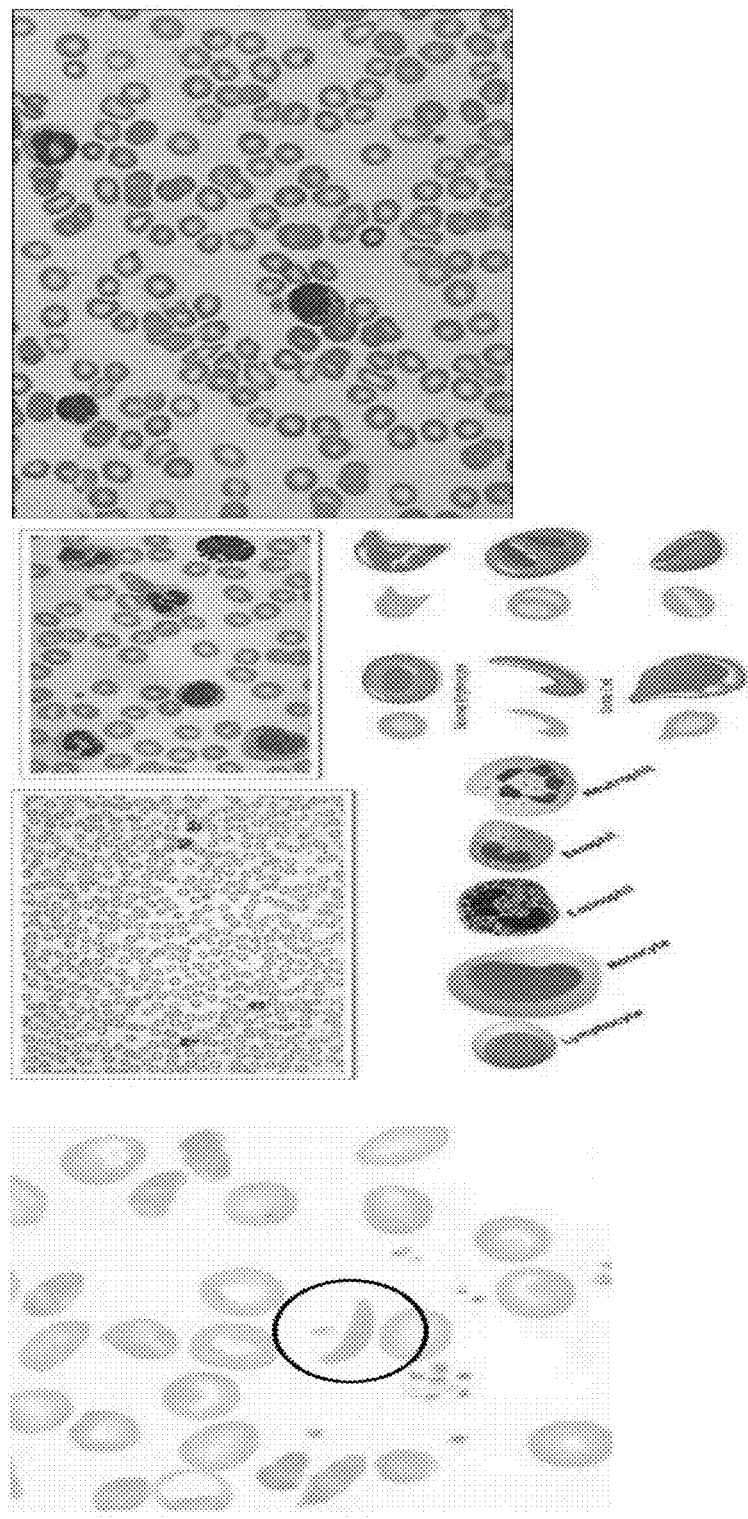
FIG. 15 depicts representative blood film showing shape of sickle RBC in SCD versus healthy subjects, in accordance with embodiments of the present invention.

FIG. 15 depicts representative blood film showing shape of sickle RBC in SCD versus healthy subjects, in accordance with embodiments of the present invention.

Figure 16:
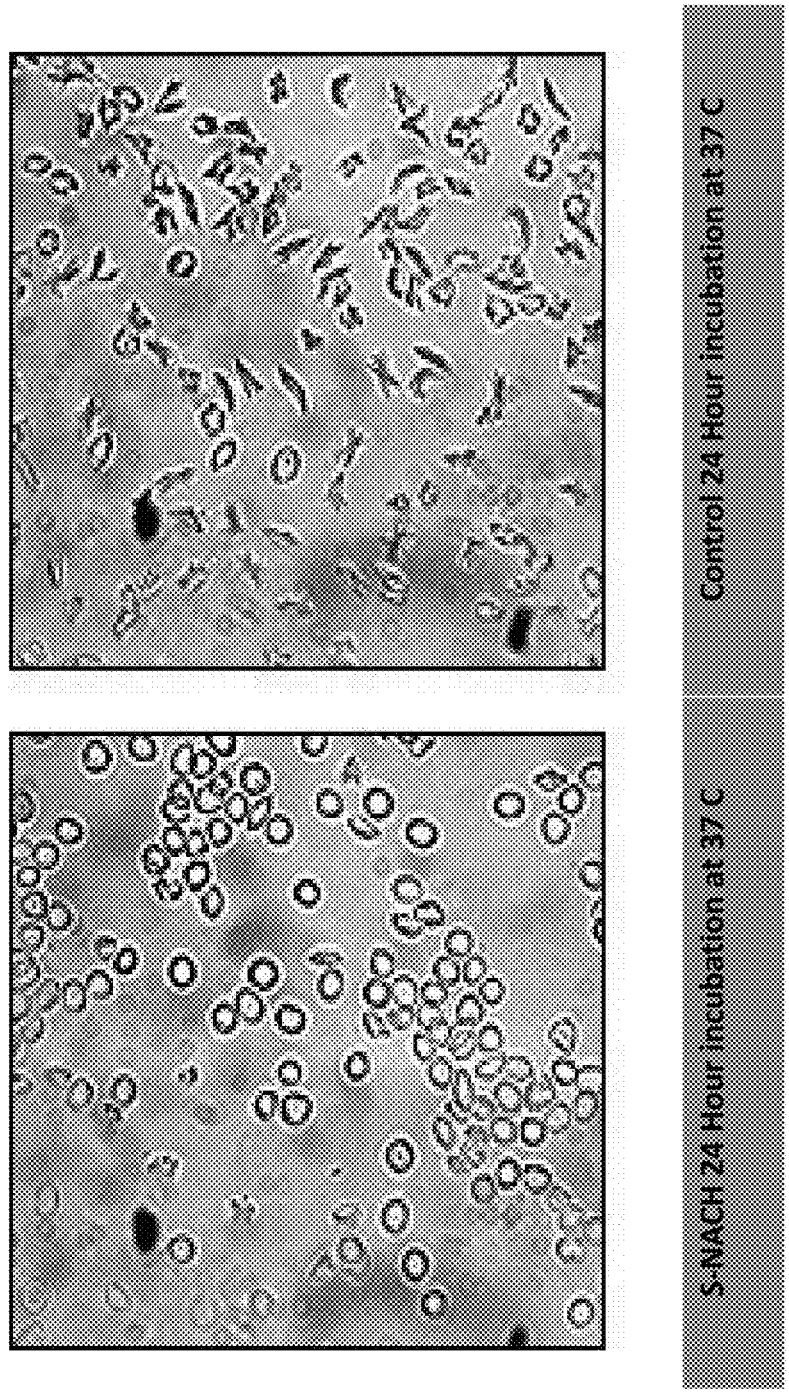
FIG. 16 illustrates the potent anti-sickling effect of SNACH in preventing and reversing sickling of RBC from SCD subjects when subjected to hypoxia for 2-24 hours at 37 degree centigrade, in accordance with embodiments of the present invention.

FIG. 16 illustrates the potent anti-sickling effect of SNACH in preventing and reversing sickling of RBC from SCD subjects when subjected to hypoxia for 2-24 hours at 37 degree centigrade, in accordance with embodiments of the present invention.

FIG. 17 illustrates the potent anti-sickling effect of SNACH in preventing and reversing sickling of RBC from SCD subjects when subjected to hypoxia for 2-4 hours at 25 degree centigrade, in accordance with embodiments of the present invention.

Figure 18:
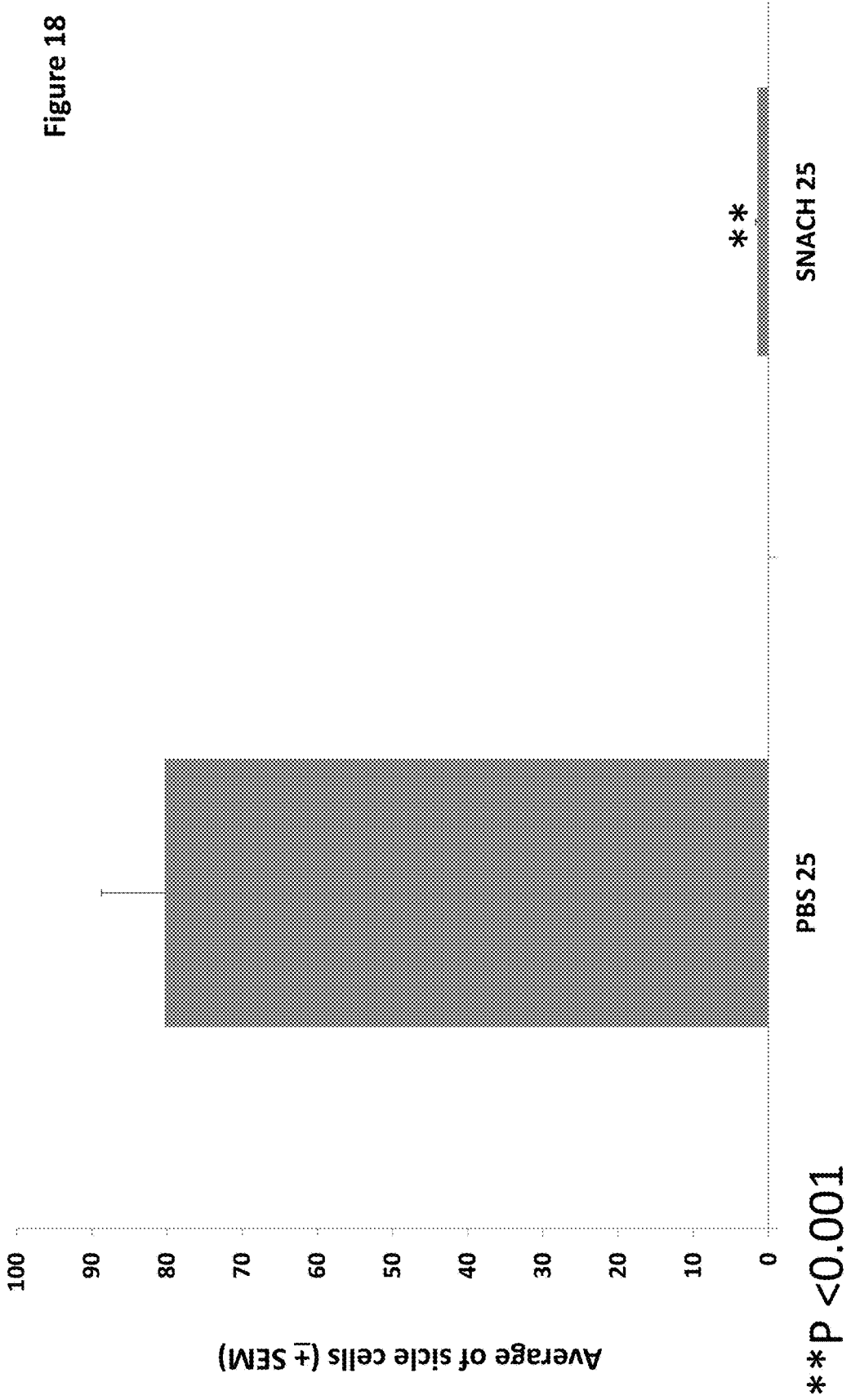
FIG. 18 illustrates average anti-sickling effect of SNACH in preventing and reversing sickling (>90% anti-sickling at 10 ug/ml blood) of RBC from SCD subjects when subjected to hypoxia for 2-4 hours at 25 degree centigrade, in accordance with embodiments of the present invention.

FIG. 18 illustrates average anti-sickling effect of SNACH in preventing and reversing sickling (>90% anti-sickling at 10 ug/ml blood) of RBC from SCD subjects when subjected to hypoxia for 2-4 hours at 25 degree centigrade, in accordance with embodiments of the present invention.

Figure 19:
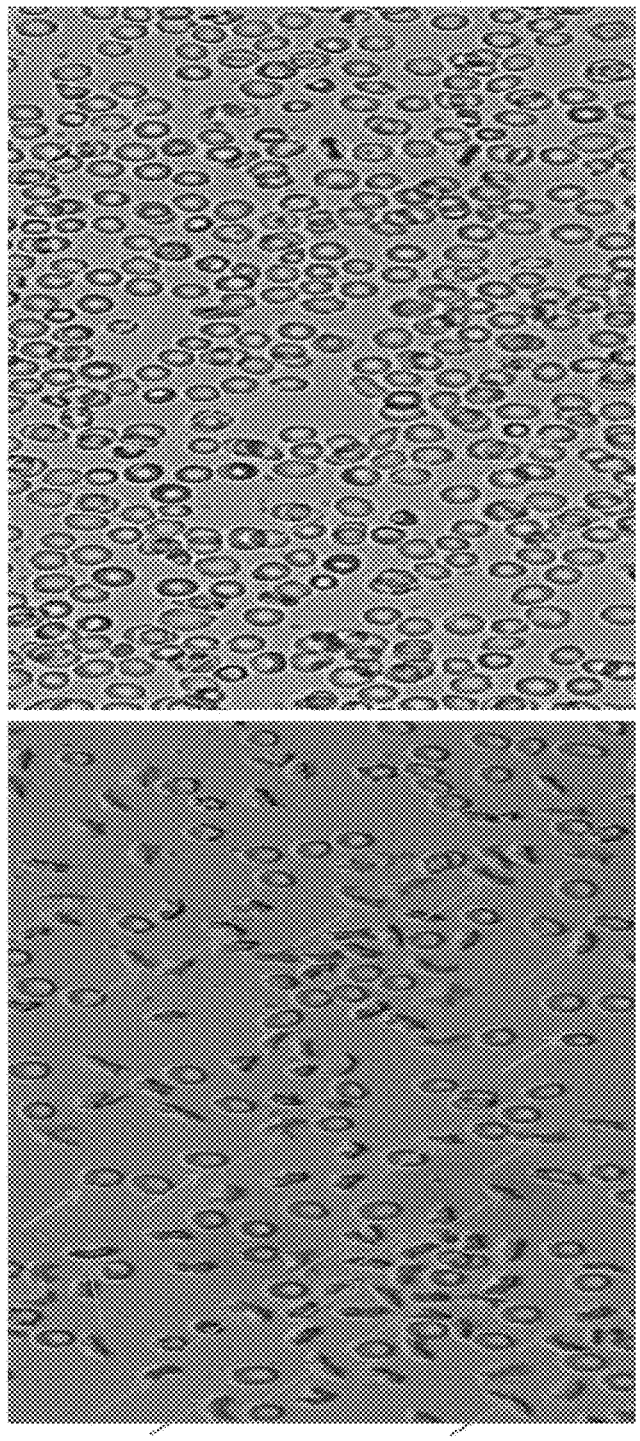
FIG. 19 depicts individual patients' during acute crisis (Patient #1) illustrating the potent anti-sickling effect of SNACH in preventing and reversing sickling of RBC from SCD subjects when subjected to hypoxia for 2-4 hours at 25 degree centigrade, in accordance with embodiments of the present invention.

FIG. 19 depicts individual patients' during acute crisis (Patient #1) illustrating the potent anti-sickling effect of SNACH in preventing and reversing sickling of RBC from SCD subjects when subjected to hypoxia for 2-4 hours at 25 degree centigrade, in accordance with embodiments of the present invention.

FIG. 20 depicts individual patients' post-acute crisis (Patient #2) illustrating the potent anti-sickling effect of SNACH in preventing and reversing sickling of RBC from SCD subjects when subjected to hypoxia for 2-4 hours at 25 degree centigrade, in accordance with embodiments of the present invention.

FIG. 21 depicts individual patients' (Patient #3) illustrating the potent anti-sickling effect of SNACH in preventing and reversing sickling of RBC from SCD subjects when subjected to hypoxia for 2-4 hours at 25 degree centigrade, in accordance with embodiments of the present invention.

FIG. 22 depicts individual patients' with once a month acute crisis (Patient #4) illustrating the potent anti-sickling effect of SNACH in preventing and reversing sickling of RBC from SCD subjects when subjected to hypoxia for 2-4 hours at 25 degree centigrade, in accordance with embodiments of the present invention.

Figure 23:
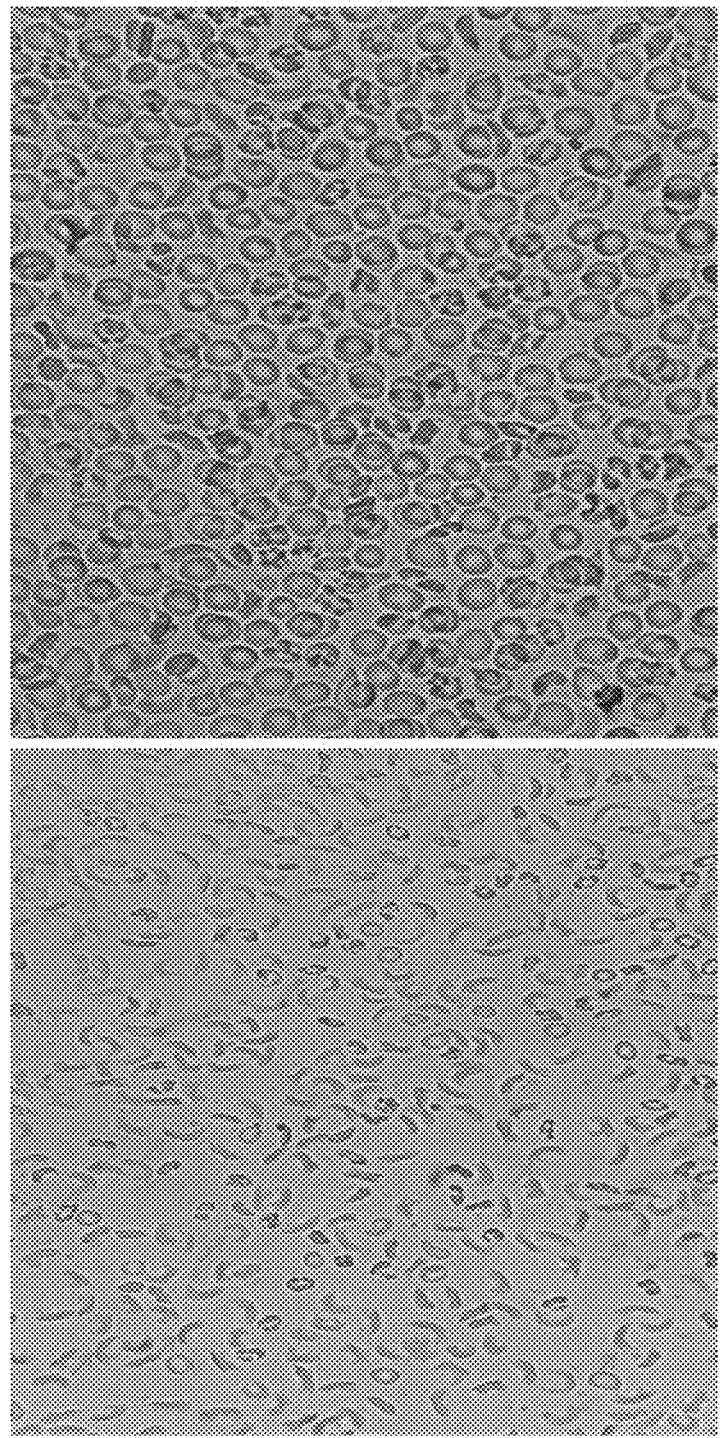
FIG. 23 depicts individual patients' with severe acute crisis (Patient #5) illustrating the potent anti-sickling effect of SNACH in preventing and reversing sickling of RBC from SCD subjects when subjected to hypoxia for 2-4 hours at 25 degree centigrade, in accordance with embodiments of the present invention.

FIG. 23 depicts individual patients' with severe acute crisis (Patient #5) illustrating the potent anti-sickling effect of SNACH in preventing and reversing sickling of RBC from SCD subjects when subjected to hypoxia for 2-4 hours at 25 degree centigrade, in accordance with embodiments of the present invention.

Figure 24:
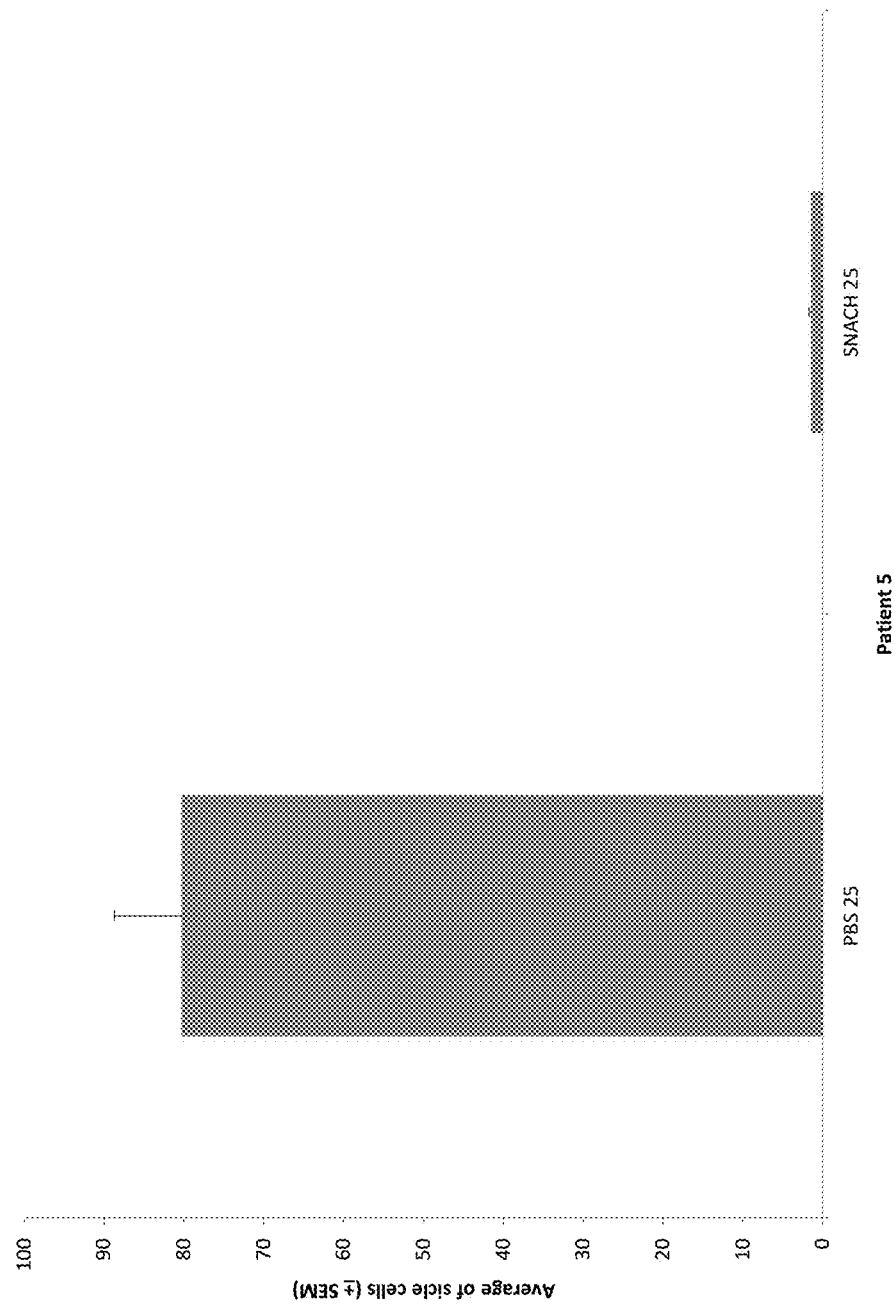
FIG. 24 illustrates average anti-sickling effect of SNACH in preventing and reversing sickling (>90% anti-sickling at 10 ug/ml blood) of RBC from SCD subject #5 when subjected to hypoxia for 2-4 hours at 25 degree centigrade, in accordance with embodiments of the present invention.

FIG. 24 illustrates average anti-sickling effect of SNACH in preventing and reversing sickling (>90% anti-sickling at 10 ug/ml blood) of RBC from SCD subject #5 when subjected to hypoxia for 2-4 hours at 25 degree centigrade, in accordance with embodiments of the present invention.

Figure 25:
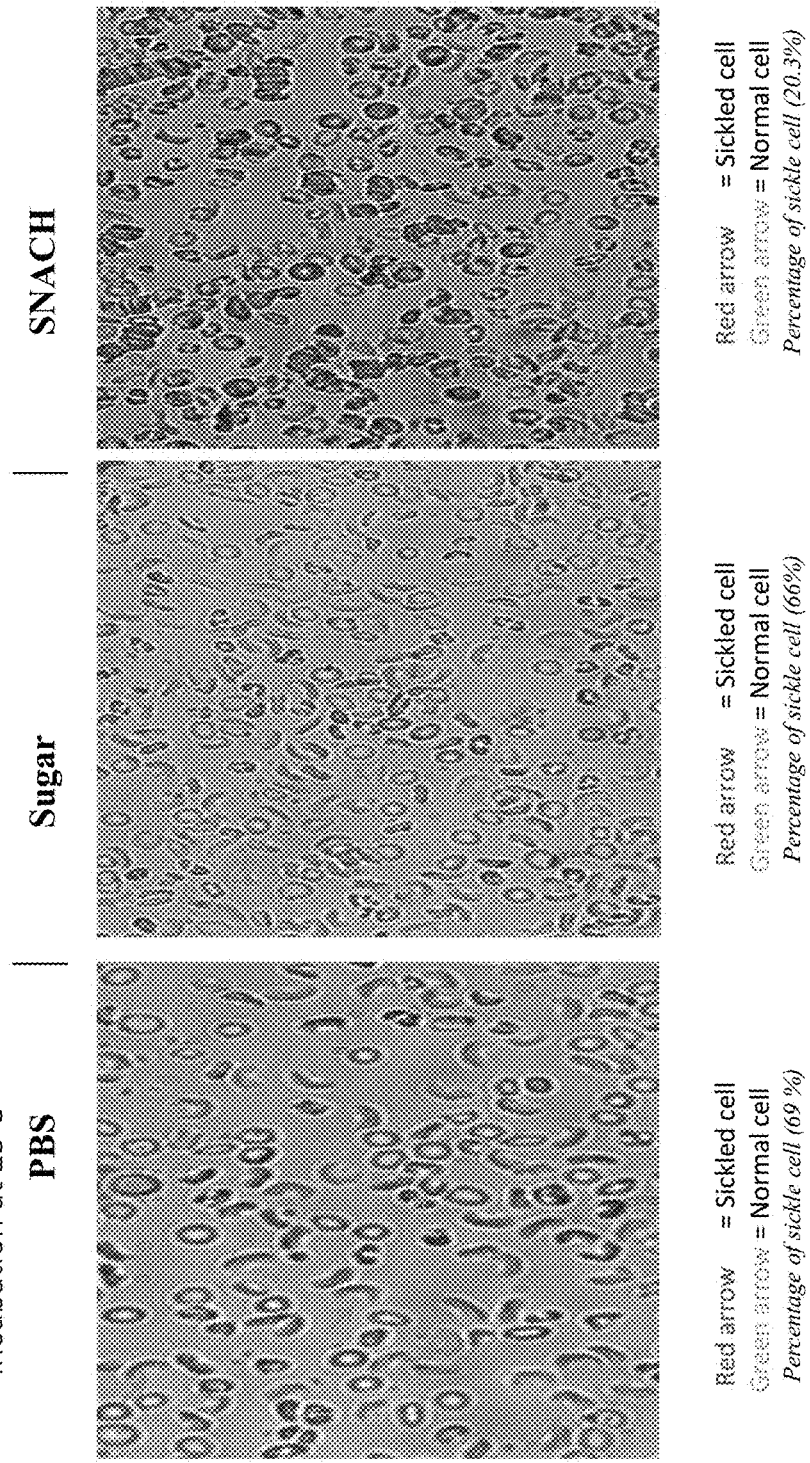
FIG. 25 depicts effect of SNACH versus Sucrose on Individual patients' with acute crisis (Patient #7) illustrating the potent anti-sickling effect of SNACH in preventing and reversing sickling of RBC from SCD subjects when subjected to hypoxia for 2-4 hours at 2.5 degree centigrade, in accordance with embodiments of the present invention.

FIG. 25 depicts effect of SNACH versus Sucrose on Individual patients' with acute crisis (Patient #7) illustrating the potent anti-sickling effect of SNACH in preventing and reversing sickling of RBC from SCD subjects when subjected to hypoxia for 2-4 hours at 25 degree centigrade, in accordance with embodiments of the present invention. In contrast, sucrose has no significant effect on the sickling.

Figure 26:
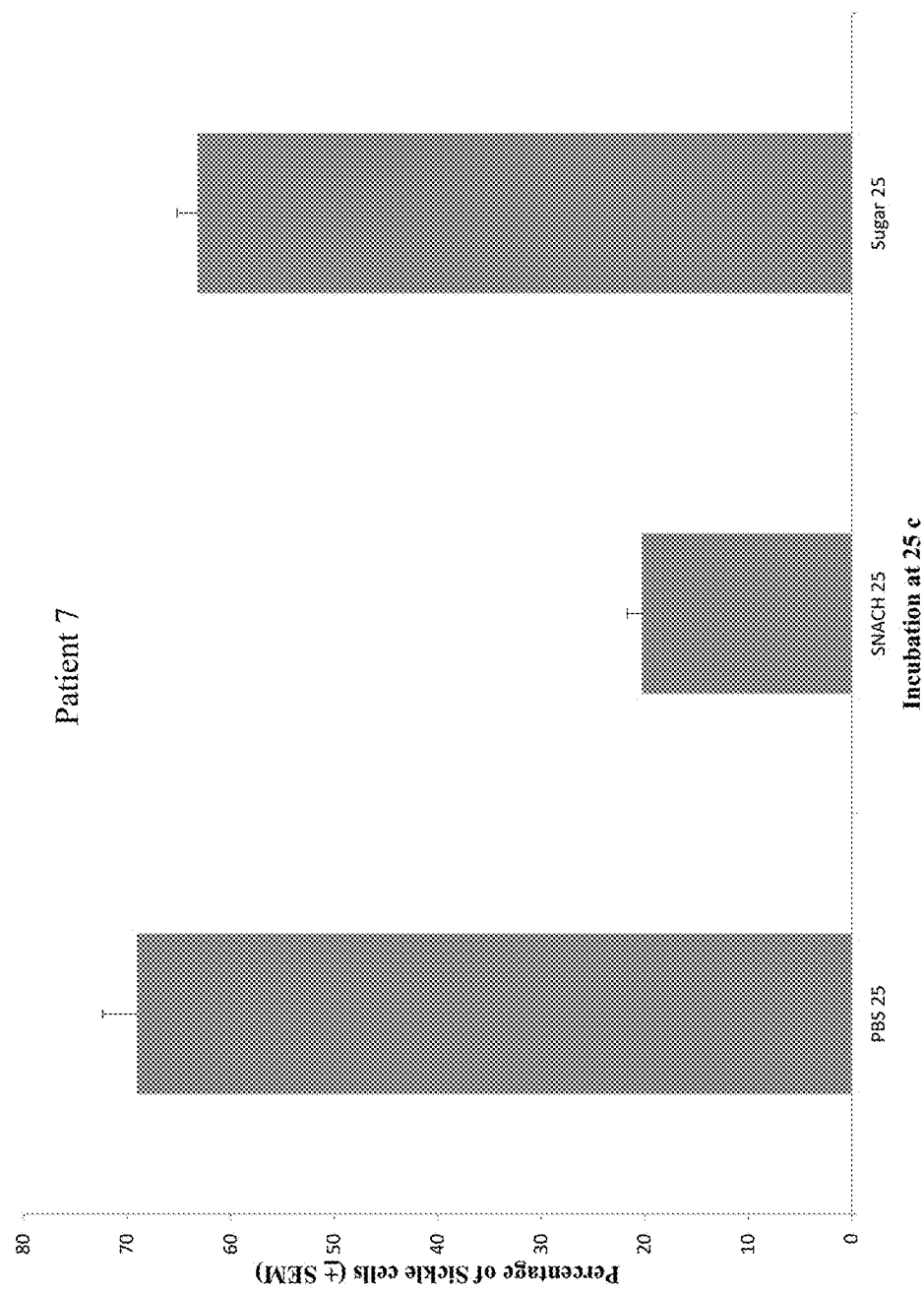
FIG. 26 depicts effect of SNACH versus Sucrose on Individual patients' with acute crisis (Patient 47) illustrating the potent anti-sickling effect of SNACH in preventing and reversing sickling of RBC from SCD subjects when subjected to hypoxia for 2-4 hours at 25 degree centigrade, in accordance with embodiments of the present invention.

FIG. 26 depicts effect of SNACH versus Sucrose on Individual patients' with acute crisis (Patient #7) illustrating the potent anti-sickling effect of SNACH in preventing and reversing sickling of RBC from SCD subjects when subjected to hypoxia for 2-4 hours at 25 degree centigrade, in accordance with embodiments of the present invention. In contrast, sucrose has no significant effect on the average % of sickle RBC over 2-4 hours.

FIG. 27 depicts a representative illustration for the effect of SNACH on RBC from healthy subjects showing no effect on the normal morphology of RBC obtained from normal subjects, in accordance with embodiments of the present invention.

Figure 28:
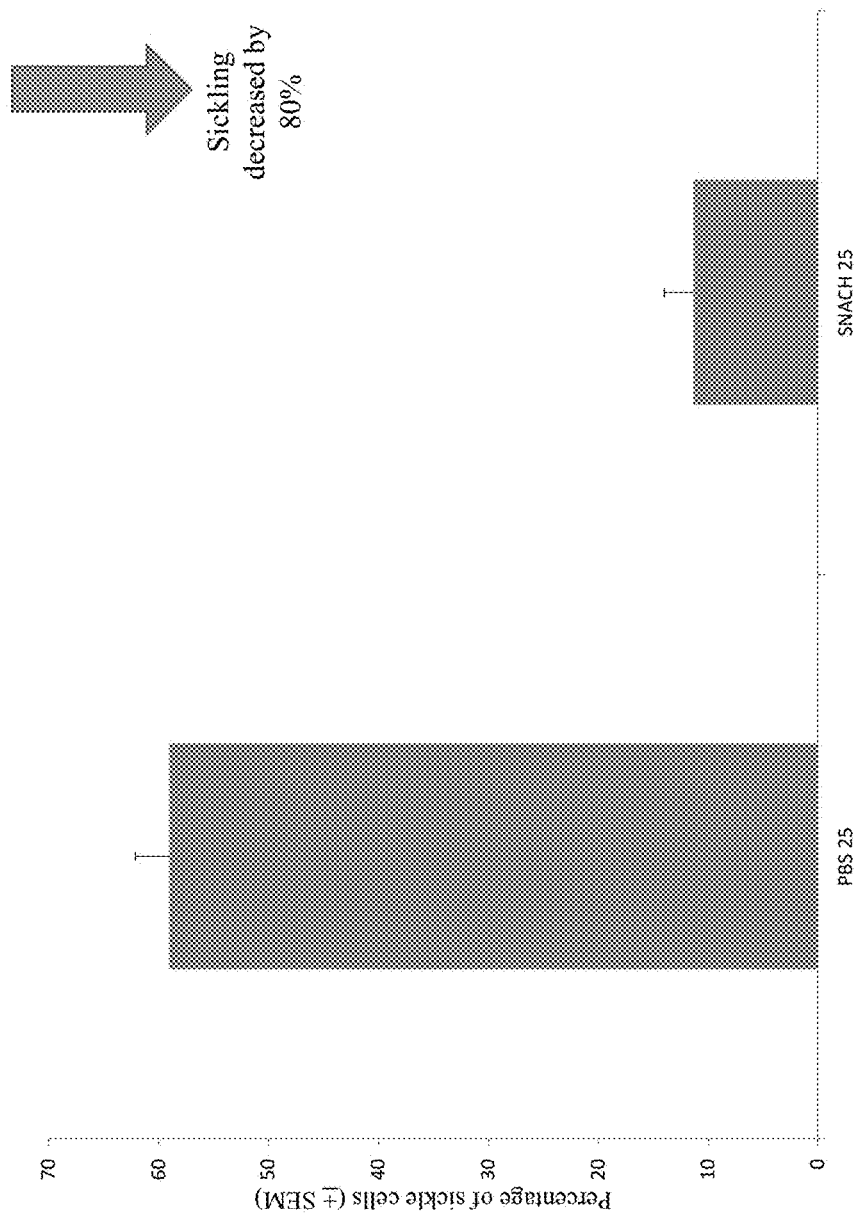
FIG. 28 depicts average of sickle cells in all 12 patients, in accordance with embodiments of the present invention.

FIG. 28 depicts average of sickle cells in all 12 patients, in accordance with embodiments of the present invention.

The present invention provides a nano-composition comprising nanoparticles, wherein the nanoparticles comprise a polycationic polymer ionically bonded to one or more polyanionic Glycosaminoglycans (GAGs), and wherein the polycationic polymer is selected from the group consisting of chitosan, methylated chitosan, poly L-Lysine, and poly L-Arginine.

In one embodiment, the polycationic polymer is ionically and covalently bonded to the one or more polyanionic GAGs.

In one embodiment, the one or more polyanionic GAGs comprise Low Molecular Weight Heparin (LMWH) and/or Sulfated Non-Anticoagulant Heparin (SNACH) derivatives, wherein the LMWH has an average molecular weight in a range of 4000 to 8000 Daltons.

In one embodiment, the one or more polyanionic GAGs comprise sulfated oligosaccharides, dermatan sulfate, heparin, heparan sulfate, chondroitin sulfate, and fucoidan, or combinations thereof.

In one embodiment, wherein the one or more polyanionic GAGs of the nanoparticles are co-encapsulated with polyphenol, thiol containing compounds, amino acids, thymoquinone, L-propionyl carnitine, disodium cromoglycate, o-vanillin, flavone, isoflavones, flavonoids, or combinations thereof.

In one embodiment, the one or more polyanionic GAGs of the nanoparticles are co-encapsulated with heterocyclic aldehyde 5-hydroxymethyl-2-furfural (5-HMF), L-Carnitine derivatives, L-Glutamine, thiol derivatives, thiosalicylate, L-Arginine, glutathione, cromoglycate, or combinations thereof.

In one embodiment, the one or more polyanionic GAGs of the nanoparticles are co-encapsulated with sphingosine-1-phosphate modulators (S1P), S1P antagonists, S1P inhibitors, or combinations thereof.

In one embodiment, the polycationic polymer comprises chitosan having an average molecular weight in a range of 5,000 to 100,000 Daltons In one embodiment, the nanoparticles are coated with a permeation enhancer.

In one embodiment, the nanoparticles have a linear size in a range of 150 to 500 nm.

In one embodiment, the nanoparticles have a positive zeta potential in a range of +10 to +50 mv or a negative zeta potential in a range of −10 to −50 mv.

The present invention provides a method of forming the nano-composition, the method comprising: ionically bonding the polycationic polymer with the one or more polyanionic GAGs to form an ionically bonded complex, followed by coating the ionically bonded complex with pluronic F-68 to form a shell of each ionically bonded nanoparticle.

In one embodiment, the method further comprises: covalently bonding the polycationic polymer with the one or more polyanionic GAGs by adding EDC (N-(3-Dimethylaminopropyl)-N'-ethylcarbodiimide hydrochloride) to the ionically bonded nanoparticles.

In one embodiment, the method further comprises: coating the nanoparticles with a permeation enhancer.

In one embodiment, the method further comprises: lyophilizing the nanoparticles; and prior to said lyophilizing the nanoparticles, adding mannitol or sucrose as a cryprotectant to the nanoparticles.

The present invention provides a method of using the nano-composition, the method comprising: administering the nano-composition to a mammal (e.g., human being) which may be a patient. In one embodiment, the mammal (e.g., human being) has a vasoocclusive disorder (e.g., sickle cell disease). In one embodiment, administering the nano-composition comprises administering the nano-composition orally, topically, or by injection.

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A nano-composition comprising nanoparticles,
   wherein the nanoparticles comprise a polycationic polymer ionically bonded to one or more polyanionic Glycosaminoglycans (GAGs),
   wherein the one or more polyanionic GAGs are co-encapsulated with: heterocyclic aldehyde 5-hydroxymethyl-2-furfural (5-HMF), at least one substance, and at least one additional substance, wherein the at least one substance is selected from the group consisting of thiosalicylate, cromoglycate, and combinations thereof, wherein the at least one additional substance is selected from the group consisting of L-Carnitine derivatives, L-Glutamine, thiol derivatives, L-Arginine, glutathione, and combinations thereof and
   wherein the polycationic polymer is selected from the group consisting of chitosan, methylated chitosan, poly L-Lysine, and poly L-Arginine.

2. The nano-composition of claim 1, wherein the polycationic polymer is ionically and covalently bonded to the one or more polyanionic GAGs.

3. The nano-composition of claim 1,
   wherein the one or more polyanionic GAGs comprise Low Molecular Weight Heparin (LMWH) and/or Sulfated Non-Anticoagulant Heparin (SNACH) derivatives, and
   wherein the LMWH has an average molecular weight in a range of 4000 Daltons to 8000 Daltons.

4. The nano-composition of claim 1, wherein the one or more polyanionic GAGs comprise the LMWH.

5. The nano-composition of claim 1, wherein the one or more polyanionic GAGs comprise the LMWH and the SNACH derivatives.

6. The nano-composition of claim 1, wherein the one or more polyanionic GAGs comprise sulfated oligosaccharides, dermatan sulfate, heparin, heparan sulfate, chondroitin sulfate, and fucoidan, or combinations thereof.

7. The nano-composition of claim 1, wherein the one or more polyanionic GAGs of the nanoparticles are co-encapsulated with polyphenol, thiol containing compounds, amino acids, thymoquinone, L-propionyl carnitine, disodium cromoglycate, o-vanillin, flavone, isoflavones, flavonoids, or combinations thereof.

8. The nano-composition of claim 1, wherein the one or more polyanionic GAGs of the nanoparticles are co-encapsulated with sphingosine-1-phosphate (S1P) modulators, S1P antagonists, S1P inhibitors, or combinations thereof.

9. The nano-composition of claim 1, wherein the polycationic polymer has an average molecular weight in a range of 5,000 Daltons to 100,000 Daltons.

10. The nano-composition of claim 1, wherein the nanoparticles are coated with a permeation enhancer.

11. The nano-composition of claim 1, wherein the nanoparticles have a linear size in a range of 150 nm to 500 nm.

12. The nano-composition of claim 1, wherein the nanoparticles have a positive zeta potential in a range of +10 mv to −50 mv or a negative zeta potential in a range of −10 mv to −50 mv.

13. A method of forming the nano-composition of claim 1, said method comprising:
    ionically bonding the polycationic polymer with the one or more polyanionic GAGs to form an ionically bonded complex, followed by coating the ionically bonded complex with pluronic F-68 to form a shell of each ionically bonded nanoparticle.

14. The method of claim 13, said method further comprising:
    covalently bonding the polycationic polymer with the one or more polyanionic GAGs by adding EDC (N-(3-Dimethylaminopropyl)-N'-ethylcarbodiimide hydrochloride) to the ionically bonded nanoparticles.

15. The method of claim 13, said method further comprising:
    coating the nanoparticles with a permeation enhancer.

16. The method of claim 13, said method further comprising:
    lyophilizing the nanoparticles; and
    prior to said lyophilizing the nanoparticles, adding mannitol or sucrose as a cryprotectant to the nanoparticles.

17. A method of using the composition of claim 1, said method comprising:
    administering the nano-composition to a human being having a vasoocclusive disorder.

18. The method of claim 17, wherein the vasoocclusive disorder is sickle cell anemia.

19. The method of claim 17, wherein said administering comprises administering the nano-composition orally, topically, or by injection.

* * * * *

UNITED STATES PATENT AND TRADEMARK OFFICE
CERTIFICATE OF CORRECTION

| | |
|---|---|
| PATENT NO. | : 9,822,190 B2 |
| APPLICATION NO. | : 15/008947 |
| DATED | : November 21, 2017 |
| INVENTOR(S) | : Shaker A. Mousa |

It is certified that error appears in the above-identified patent and that said Letters Patent is hereby corrected as shown below:

In the Claims

Column 16, Line 15, Claim 12 change "-" to "+"

Signed and Sealed this
Tenth Day of July, 2018

Andrei Iancu
*Director of the United States Patent and Trademark Office*